US011510408B2

(12) United States Patent
Yoshida et al.

(10) Patent No.: US 11,510,408 B2
(45) Date of Patent: Nov. 29, 2022

(54) CRYOPRESERVATION JIG FOR CRYOPRESERVING CELLS OR TISSUES

(71) Applicant: MITSUBISHI PAPER MILLS LIMITED, Tokyo (JP)

(72) Inventors: Kakeru Yoshida, Tokyo (JP); Atsushi Matsuzawa, Tokyo (JP); Yukio Tokunaga, Tokyo (JP)

(73) Assignee: MITSUBISHI PAPER MILLS LIMITED, Tokyo (JP)

( * ) Notice: Subject to any disclaimer, the term of this patent is extended or adjusted under 35 U.S.C. 154(b) by 399 days.

(21) Appl. No.: 16/621,337

(22) PCT Filed: Jun. 8, 2018

(86) PCT No.: PCT/JP2018/022105
§ 371 (c)(1),
(2) Date: Dec. 11, 2019

(87) PCT Pub. No.: WO2018/230477
PCT Pub. Date: Dec. 20, 2018

(65) Prior Publication Data
US 2020/0113176 A1   Apr. 16, 2020

(30) Foreign Application Priority Data

Jun. 12, 2017 (JP) ............................. JP2017-114822
Feb. 27, 2018 (JP) ............................. JP2018-032654
Mar. 23, 2018 (JP) ............................. JP2018-056780

(51) Int. Cl.
*A01N 1/02* (2006.01)

(52) U.S. Cl.
CPC ......... *A01N 1/0268* (2013.01); *A01N 1/0221* (2013.01); *A01N 1/0242* (2013.01)

(58) Field of Classification Search
None
See application file for complete search history.

(56) References Cited

U.S. PATENT DOCUMENTS 5,310,674 A    5/1994  Weinreb et al.
5,506,141 A *  4/1996  Weinreb ................. G01N 15/10
                                                        435/308.1
10,039,278 B2 * 8/2018  Matsuzawa .............. C12M 1/00
10,624,335 B2 * 4/2020  Matsuzawa .......... A01N 1/0268
2012/0040450 A1 * 2/2012  Clarke ................ A01N 1/0242
                                                        435/307.1
2016/0235056 A1   8/2016  Momozawa et al.
2018/0000067 A1 * 1/2018  Nagashima ............. C12N 1/04

FOREIGN PATENT DOCUMENTS

| JP | 3044323 B1 | 5/2000 |
| JP | 2002-315573 A | 10/2002 |
| JP | 2006-271395 A | 10/2006 |
| JP | 2008-005846 A | 1/2008 |
| JP | 2014-183757 A | 10/2014 |
| JP | 2015-142523 A | 8/2015 |
| JP | 5781621 B2 | 9/2015 |
| JP | 5798633 B2 | 10/2015 |
| JP | 2015/226497 | * 12/2015 |
| JP | 2015-226497 A | 12/2015 |
| JP | 3202359 U | 1/2016 |
| JP | 2017-060457 A | 3/2017 |
| WO | 2011/070973 A1 | 6/2011 |
| WO | WO 2011/070973 | * 6/2011 |
| WO | 2015/033926 A1 | 3/2015 |
| WO | WO 2015/033926 | * 3/2015 |
| WO | 2015/064380 A1 | 5/2015 |

OTHER PUBLICATIONS

P. L. Steponkus et al., "Cryopreservation of *Drosophila melanogaster* embryos", Nature, May 10, 1990, vol. 345, pp. 170-172 (3 pages).
International Search Report issued in International Application No. PCT/JP2018/022105, dated Sep. 4, 2018 (1 page).
Written Opinion issued in International Application No. PCT/JP2018/022105, dated Sep. 4, 2018 (5 pages).
Office Action issued in Korean Application No. 2019-7035776, dated Jan. 21, 2021 (5 pages).
Extended European Search Report for counterpart European Application No. 18818541.7, dated Feb. 17, 2021 (7 pages).

* cited by examiner

*Primary Examiner* — Ralph J Gitomer
(74) *Attorney, Agent, or Firm* — Osha Bergman Watanabe & Burton LLP

(57) ABSTRACT

The present invention aims to provide a device for cryopreservation which enables easy and reliable cryopreservation of a cell or tissue. The device for cryopreservation of a cell or tissue of the present invention includes a deposition part on which a cell or tissue is to be deposited together with a preservation solution, wherein a surface of the deposition part includes a protrusion for holding a cell or tissue and a recess for storing a preservation solution.

4 Claims, 8 Drawing Sheets

CRYOPRESERVATION JIG FOR CRYOPRESERVING CELLS OR TISSUES

TECHNICAL FIELD

The present invention relates to a device for cryopreservation of cells or tissues for use in cryopreservation of cells or tissues.

BACKGROUND ART

Excellent preservation techniques for cells or tissues are desired in various industrial fields. For example, in the bovine embryo transfer technology, embryos are cryopreserved in advance and thawed and transferred in time with the estrus cycle of a recipient cow. In the human fertility treatment, eggs or ovaries are harvested from a woman's body and cryopreserved until an appropriate timing for transplantation, and the cryopreserved eggs or ovaries are thawed before the use in transplantation.

In general, cells or tissues harvested from living bodies gradually become inactive even in a culture medium, and hence long-term culture of cells or tissues in vitro is undesirable. For this reason, techniques for long-term preservation of cells or tissues without the loss of biological activity are essential. Excellent preservation techniques enable more accurate analysis of cells or tissues harvested. Such excellent preservation techniques also enable transplantation of cells or tissues with their biological activity kept at a higher level, thus likely resulting in an improvement in the engraftment rate. The techniques also enable in-advance production and preservation of artificial tissues for transplantation, such as skins cultured in vitro and what they call cell sheets formed in vitro, and storage thereof until needed. Therefore, such excellent preservation techniques are expected to bring great advantages not only in the medical science fields but also in the industrial fields.

One of known methods for preserving cells or tissues is slow freezing, for example. In this method, cells or tissues are immersed in a preservation solution prepared by adding a cryoprotectant to a physiological solution such as phosphate buffered saline. Examples of the cryoprotectant include compounds such as glycerol and ethylene glycol. The cells or tissues immersed in the preservation solution are cooled down to $-30°$ C. to $-35°$ C. at a relatively slow cooling rate (for example, $0.3°$ C. to $0.5°$ C./min), and thereby the solution inside and outside the cells or tissues are sufficiently cooled and become viscous. Further cooling down the cells or tissues in such a state in the preservation solution to the temperature of liquid nitrogen ($-196°$ C.) allows a slight amount of the solution both inside and outside (surrounding) the cells or tissues to become a solid while the amorphous state thereof is maintained, that is, to vitrify. The vitrification (i.e., solidification) of the solution inside and outside the cells or tissues substantially immobilizes the molecules. Thus, the vitrified cells or tissues can be semipermanently preserved in liquid nitrogen.

However, since the slow freezing requires relatively slow-rate cooling, the procedure of cryopreservation takes a long time. Further, this technique disadvantageously requires a device or jig for controlling the cooling rate. In addition, the slow freezing cannot avoid formation of ice crystals in the preservation solution outside the cells or tissues, which may cause physical damage to the cells or tissues.

One proposed solution to the problems of the slow freezing is the vitrification method. The vitrification method is a technique using a principle that addition of a large amount of a cryoprotectant, such as glycerol, ethylene glycol, or dimethyl sulfoxide (DMSO), to a preservation solution decreases the freezing point of the preservation solution, thereby restraining formation of ice crystals at sub-zero temperatures. When quickly cooled in liquid nitrogen, the preservation solution can solidify without formation of ice crystals. This solidification is called vitrification. The preservation solution containing a large amount of a cryoprotectant is called a vitrification solution.

The specific procedure of the vitrification method is to immerse cells or tissues in a preservation solution containing a large amount of a cryoprotectant and to cool them at the temperature of liquid nitrogen ($-196°$ C.). Since the vitrification method is such a simple and quick process, it advantageously does not require a long-term procedure of cryopreservation or the use of any temperature-controlling device or jig.

The vitrification method does not cause formation of ice crystals either inside or outside the cells or tissues, and thus can avoid physical damage (freezing damage) to the cells or tissues at the time of freezing and thawing. However, successful vitrification requires a highly concentrated cryoprotectant in a preservation solution for vitrification. Yet, a highly concentrated cryoprotectant in a preservation solution is known to be high chemically toxic to cells or tissues.

Based on the background described above, the exposure time of cells or tissues to the preservation solution (i.e., the time until freezing) is preferably short in cryopreservation of the cells or tissues. In addition, in view of increasing the freezing speed, a smaller amount of the preservation solution around cells or tissues is better during cryopreservation of the cells or tissues. The smaller the amount of the preservation solution present around cells or tissues, the lower the heat capacity of the object to be frozen and the faster the freezing speed of the cells or tissues, which is preferred for vitrification. Further, a smaller amount of the preservation solution present around cells or tissues is also preferred because the preservation solution is quickly diluted in a thawing solution during thawing of the frozen cells or tissues, and re-formation of ice crystals in the cells or tissues can be inhibited. A smaller amount of the preservation solution present around cells or tissues is also preferred because the concentration of a cryoprotectant that gets mixed with a thawing solution during thawing can be reduced, which can thus alleviate the toxicity derived from the cryoprotectant.

Various examples of cryopreservation of cells or tissues by the vitrification method have been reported using various methods and various cells or tissues. For example, Patent Literature 1 discloses that application of the vitrification method to reproductive or somatic cells of animal or human origin is very useful in terms of the cell viability after cryopreservation and thawing.

The vitrification method is a technique which has been developed mainly using human reproductive cells. More recently, its application to iPS or ES cells has also been widely examined. Non-Patent Literature 1 discloses the effectiveness of the vitrification method in preservation of *Drosophila* embryos. Patent Literature 2 discloses the effectiveness of the vitrification method in preservation of plant culture cells and tissues. As mentioned here, the vitrification method is known to be useful for preservation of a wide range and different kinds of cells and tissues.

Patent Literature 3 and Patent Literature 4 propose a cryopreservation method, what is called the Cryotop method, used in the field of human fertility treatment. This method uses a tool for cryopreservation of eggs including a flexible, clear and colorless film strip as an egg-holding strip, and includes depositing eggs or embryos together with a very small amount of a preservation solution on the film under a microscope.

Patent Literature 5 and Patent Literature 6 each disclose a device for cryopreservation including an elongated holding portion to which a living cell is to be attached, wherein a recess for accommodating the cell is provided in the holding portion in the longitudinal direction thereof.

Patent Literature 7 proposes a cryopreservation method including depositing eggs or embryos together with a preservation solution containing a large amount of a cryoprotectant on a material for removing a preservation solution and removing an excess preservation solution surrounding the eggs or embryos by downward suction. Examples of the material for removing a preservation solution include wire mesh and perforated films made of natural substance, such as paper, or synthetic resin. Devices for cryopreservation which allow the removal of an excess preservation solution and can improve the working efficiency during deposition of cells have also been proposed. For example, Patent Literature 8 discloses a preservation solution absorber with a specific haze value, and Patent Literature 9, Patent Literature 10, and the like each disclose a device for vitrification cryopreservation including a preservation solution absorber having a porous sintered body or a porous structure formed of a material having a specific refractive index.

Devices for cryopreservation which can improve the working efficiency when depositing a cell or tissue are as described above. As for devices for cryopreservation which can improve the working efficiency when releasing a cell or tissue, for example, Patent Literature 11 discloses a device for cryopreservation of a cell or tissue, including a layer containing a water-soluble polymeric compound on an outermost surface of a deposition part on which a cell or tissue is to be deposited. Patent Literature 12 discloses a cell container having an inner surface with fine protrusions formed thereon in order to prevent attachment of cells to the inner surface of the container.

CITATION LIST

Patent Literature

Patent Literature 1: JP 3044323 B
Patent Literature 2: JP 2008-5846 A
Patent Literature 3: JP 2002-315573 A
Patent Literature 4: JP 2006-271395 A
Patent Literature 5: JP 5781621 B
Patent Literature 6: JP 5798633 B
Patent Literature 7: WO 2011/070973
Patent Literature 8: JP 2014-183757 A
Patent Literature 9: JP 2015-142523 A
Patent Literature 10: WO 2015/064380
Patent Literature 11: JP 2017-60457 A
Patent Literature 12: JP 2015-226497 A Non-Patent Literature Non-Patent Literature 1: Steponkus et al., Nature 345: 170-172 (1990)

SUMMARY OF INVENTION

Technical Problem

Patent Literature 3 and Patent Literature 4 each propose a method for cryopreserving eggs or embryos together with a small amount of a preservation solution to provide excellent viability by limiting the width of a film on which eggs or embryos are to be deposited. However, when thawing frozen eggs or embryos, the eggs or embryos on the film often adhere to the film surface due to the state or the like of the frozen object, and recovering the eggs or embryos disadvantageously thus requires high-level skills. Further, as a worker cryopreserves eggs or embryos with as small as possible amount of a preservation solution, disadvantageously, the eggs or embryos strongly adhere to the film surface when thawing them from the frozen state.

Patent Literature 5 and Patent Literature 6 each propose a method of reducing dropping off of cells during freezing by providing a recess for accommodating cells in a holding portion to which cells are to be attached, but these methods still require high-level skills for recovering the cells, as in Patent Literature 3 and Patent Literature 4.

The method proposed in Patent Literature 7 is for cryopreservation of eggs or embryos by removing an excess preservation solution surrounding these reproductive cells by suction from the bottom of a material for removing a preservation solution. However, the eggs or embryos adhere to the material for removing a preservation solution when thawing them from the frozen state, and high-level skills are thus required for recovering these cells, as in Patent Literature 3 and Patent Literature 4. In Patent Literatures 8 to 10, unlike Patent Literature 7 described above, a worker is not required to remove an excess preservation solution surrounding eggs or embryos, so that good working efficiency is achieved. However, the absorption of the preservation solution by a preservation solution absorber causes particularly strong adhesion of the eggs or embryos to the preservation solution absorber. Thus, high-level skills are required for recovering these eggs or embryos.

Patent Literature 11 proposes a method for forming a layer containing a water-soluble polymeric compound on a deposition part of a device for cryopreservation in order to prevent cells or tissues from adhering to the deposition part when thawing from the frozen state. Improving the recoverability of cells or tissues when thawing them from the frozen state is a permanent issue, and a further improvement has been desired.

Patent Literature 12 proposes a method of inhibiting attachment of cells to an inner surface of a cell container such as a storage vial in which cells are stored with a preservation solution, by forming fine protrusions on the inner surface of the cell container. However, the above technique is to inhibit attachment of the cells but is not intended to release and use the cells that have been purposely attached to be stored. In the case of what is called the Cryotop method in which a very small number (about 1 to 3 in many cases) of cells or tissues are deposited together with a very small amount of a preservation solution, not only smooth recovery of cells or tissues without strong adhesion of the cells or tissues during thawing but also reliable holding of the cells or tissues on a cryopreservation device during cryopreservation are required.

A main object of the present invention is to provide a device for cryopreservation of a cell or tissue which enables easy and reliable cryopreservation of a cell or tissue. Specifically, the present invention aims to provide a device for cryopreservation which can reliably hold a cell or tissue deposited on a surface of a deposition part and can reduce the amount of an excess preservation solution surrounding the deposited cell or tissue when the cell or tissue is cryopreserved by being immersed in the preservation solution and deposited on the deposition part of the device for cryopreservation, and which further enables quick recovery of the cell or tissue when thawing from the frozen state.

Solution to Problem

As a result of intensive studies to solve the above problems, the present inventors found out that a device for cryopreservation of a cell or tissue (herein, the "device for cryopreservation of a cell or tissue" is also referred to simply as a "device for cryopreservation") having the following configuration can solve the above problems.

(1) A device for cryopreservation of a cell or tissue including: a deposition part on which a cell or tissue is to be deposited together with a preservation solution, wherein a surface of the deposition part includes a protrusion for holding a cell or tissue and a recess for storing a preservation solution.

(2) The device for cryopreservation of a cell or tissue according to (1) above, wherein the protrusion for holding a cell or tissue has a height that is $1/100$ or more and less than $1/2$ of an average diameter of a cell or tissue.

(3) The device for cryopreservation of a cell or tissue according to (1) above, wherein the surface of the deposition part on which a cell or tissue is to be deposited together with a preservation solution has an arithmetic average roughness Ra of 1.0 μm or more.

(4) The device for cryopreservation of a cell or tissue according to any one of (1) to (3) above, wherein the deposition part has a preservation solution absorber.

Advantageous Effects of Invention

The invention described above can provide a device for cryopreservation which enables easy removal of an excess preservation solution surrounding a cell or tissue attached dropwise to the deposition part, and allows the cell or tissue to be reliably held on the surface of the deposition part in the freezing procedure. The device for cryopreservation further enables quick recovery of the cell or tissue in the thawing procedure. Use of the device for cryopreservation of the present invention enables an easy and reliable cryopreservation of a cell or tissue.

DESCRIPTION OF EMBODIMENTS

Figure 1:
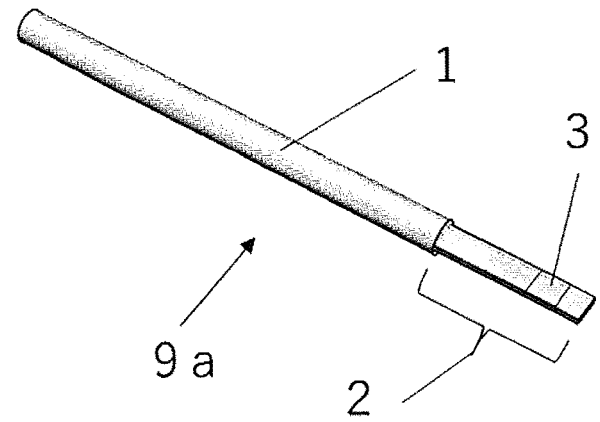
FIG. 1 is an overall view showing an exemplary device for cryopreservation of a cell or tissue of the present invention.

The device for cryopreservation of the present invention is used for cryopreserving a cell or tissue. The "cell" herein encompasses not only a single cell but also a biological cell population composed of multiple cells. The cell population composed of multiple cells may be a cell population composed of a single kind of cells or may be a cell population composed of multiple kinds of cells. The tissue may be composed of a single kind of cells or may be composed of multiple kinds of cells, or may contain a non-cellular substance like an extracellular matrix in addition to cells.

The "cryopreservation" herein encompasses a series of procedures of freezing of a cell or tissue using cryogenic refrigerant, storing of the cell or tissue in cryogenic refrigerant, and thawing of the cell or tissue in a thawing solution.

The device for cryopreservation of the present invention is used for cryopreservation, preferably for vitrification cryopreservation. Specifically, the device for cryopreservation of the present invention is to be used in a process including immersing and freezing a device for cryopreservation including a deposition part holding a cell or tissue in a coolant such as liquid nitrogen. The cell or tissue deposited on the deposition part is thawed by taking out the cell or tissue together with the device for cryopreservation from the coolant and immersing them into a thawing solution.

The use of the device for cryopreservation of the present invention allows a cell or tissue to be reliably held on a surface of the deposition part during cryopreservation. The preservation solution dropped with a cell or tissue is stored below the deposited cell or tissue, so that there is less excess preservation solution surrounding the cell or tissue, and the cell or tissue can be cryopreserved with good viability. Further, when thawing the cryopreserved cell or tissue, a preservation solution between the cell or tissue deposited on the deposition part and the surface of the deposition part is thawed from the vitrification state and quickly recovers its fluidity. As the preservation solution is diluted in the thawing solution, the cell or tissue can be easily released and recovered from the surface of the deposition part. In other words, the use of the device for cryopreservation of the present invention enables easy and reliable cryopreservation of a cell or tissue. The device for cryopreservation of a cell or tissue of the present invention can be said in different words, such as a tool for cryopreservation of a cell or tissue, a tool for preservation of a cell or tissue, an instrument for cryopreservation of a cell or tissue, and an instrument for preservation of a cell or tissue.

In the device for cryopreservation of the present invention, the surface of the deposition part on which a cell or tissue is to be deposited includes a protrusion for holding a cell or tissue and a recess for storing a preservation solution. When a cell or tissue is attached dropwise together with a preservation solution to the surface of the deposition part in the freezing procedure, the protrusion/recess configuration on the surface of the deposition part inhibits spread of the preservation solution. This prevents a significant shift of the deposited cell or tissue, and enables easy dropwise attachment of the cell or tissue with a pipette or the like. The protrusion on the surface of the deposition part can reliably hold the cell or tissue. Further, the preservation solution that was attached dropwise with the cell or tissue is stored in the recess formed below the deposited cell or tissue, so that an excess preservation solution surrounding the cell or tissue can be reduced, enabling quick vitrification. Meanwhile, when thawing the cell or tissue in the thawing procedure, the preservation solution stored (frozen) between the cell or tissue and the surface of the deposition part is thawed from the vitrified state, recovers its fluidity, and is diluted in a thawing solution, so that the cell or tissue can be easily released and recovered from the surface of the deposition part.

When the deposition part of the device for cryopreservation of the present invention has a preservation solution absorber, and the surface of the preservation solution absorber has a configuration of the present invention which includes a protrusion for holding a cell or tissue and a recess for storing a preservation solution, not only the above effects can be obtained but also the preservation solution absorber absorbs an excess preservation solution, thus eliminating the need for additional procedures of removing the excess preservation solution. This significantly improves the working efficiency. The cell or tissue after such a procedure is covered with a very small amount of the preservation solution and thus can be quickly frozen in the freezing procedure. The vitrification method described above has the disadvantage of chemical toxicity due to a large amount of cryoprotectant contained in the preservation solution. With the device for cryopreservation in which the deposition part has a preservation solution absorber, the amount of the preservation solution around the deposited cell or tissue is very small, so that an improved viability of the cell or tissue is expected.

The following describes the configuration of the device for cryopreservation of the present invention.

In the device for cryopreservation of the present invention, the surface of the deposition part on which a cell or tissue is to be deposited includes a protrusion for holding a cell or tissue and a recess for storing a preservation solution. Here, the surface of the deposition part on which a cell or tissue is to be deposited corresponds to a surface portion on which a cell or tissue is actually to be deposited together with a preservation solution.

In the device for cryopreservation of the present invention, the deposition part on which a cell or tissue is to be deposited may have any shape as long as a cell or tissue can be deposited thereon. Preferably, the deposition part has a substantially sheet-like shape. Such a device for cryopreservation including a deposition part having a substantially sheet-like shape is one preferred embodiment of the present invention. The "substantially sheet-like shape" herein means a shape having a flat surface in a macro perspective. Examples include shapes such as a flat sheet-like shape, a curved sheet-like shape, a corrugated sheet-like shape, and a V-shaped sheet-like shape.

The protrusion for holding a cell or tissue on the deposition part of the present invention corresponds to a structural portion with which the deposited cell or tissues come into contact. The deposition part includes at least one protrusion for a cell or tissue to be deposited, and may include multiple protrusions. Preferably, the deposition part includes two or more protrusions for one cell or tissue to be deposited. Since the protrusion is a structure for the purpose of holding a deposited cell or tissue, for example, the protrusion may hold a cell via a preservation solution around the cell, without direct contact between a surface of the protrusion and the cell or tissue.

The recess for storing a preservation solution in the deposition part of the present invention can preferably store a preservation solution without contact between a surface of the recess and the cell. The deposition part includes at least one recess for a cell to be deposited, and may include multiple recesses. When the device for cryopreservation includes multiple deposition parts, one or more recesses for storing a preservation solution in each deposition part may be connected together.

It is important that the protrusion is present where a cell or tissue (hereinafter also described as a "deposition target") is deposited together with a preservation solution. Thus, while there may be one site where multiple protrusions are gathered or there may be multiple sites where multiple protrusions are gathered, the multiple protrusions are preferably arranged in a state in which a cell or tissue as a deposition target is held by the multiple protrusions such that the deposition target can be reliably held by the protrusions. Specifically, the pattern pitch between the protrusions is preferably 95% or less of an average diameter of a deposition target. The pattern pitch between the protrusions is the distance between the centers of the closest protrusions when viewed from the top. The protrusion(s) may or may not be present where a cell or tissue is not to be deposited.

The height of the protrusion (i.e., the depth of the recess) for holding a cell or tissue on the deposition part of the present invention may be suitably selected according to the size of a cell or tissue to be deposited, but is preferably 100 nm or more. When the height of the protrusion is lower than 100 nm, the amount of a preservation solution to be stored in the recess may be insufficient, failing to achieve the effect.

In the present invention, the protrusion for holding a cell or tissue preferably has a height that is $1/100$ or more and less than $1/2$ of an average diameter of a cell or tissue to be deposited. This enables easy release and recovery of the cell or tissue in the thawing procedure. In the present invention, the protrusion formed on the surface of the deposition part for a cell or tissue reduces the contact area between the deposition part and a deposition target, and can thus facilitate release of the deposition target from the deposition part of the device for cryopreservation in the thawing procedure. Such an effect is particularly significant when the protrusion has a height that is $1/100$ or more of an average diameter of a cell or tissue. In the present invention, the average diameter of a cell or tissues is an average equivalent spherical diameter. When a cell or tissue is a sphere, the equivalent spherical diameter refers to the diameter of the sphere. When a cell or tissue to be deposited is not a sphere, the sphere-equivalent diameter is determined from the volume of the cell or tissue, and the resulting value is used as the equivalent spherical diameter. When a single cell or tissue is deposited, the equivalent spherical diameter of the cell or tissue is used as the average diameter.

In one embodiment, the device for cryopreservation of the present invention is suitably used as a device for cryopreservation of a cell or tissue preferably having an average diameter of 1 to 500 µm.

When the protrusion has a height that is ½ or more of the average diameter of a cell or tissue, the deposition target may not be easily released from the device for cryopreservation in the thawing procedure. Although the reason is uncertain, generally, cells or tissues are deposited by procedure of incubation experts, together with a small amount of a preservation solution, on the deposition part in order to reduce the impact of chemical toxicity of a cryoprotectant. When the protrusion has a height that is ½ or more of the average diameter of a cell or tissue, it is difficult to freeze a cell or tissue with an appropriate liquid film formed between the protrusion and the cell or tissue, and good thawing releasability may not be achieved. When such a device for cryopreservation is used, an embodiment of the present invention is a cryopreservation method including depositing a cell or tissue on a device for cryopreservation and cryopreserving the cell or tissue, wherein the device for cryopreservation includes a deposition part on which a cell or tissue is to be deposited, a surface of the deposition part includes a protrusion for holding a cell or tissue, and a recess for storing a preservation solution, and the protrusion for holding a cell or tissue has a height that is $1/100$ or more and less than ½ of an average diameter of a cell or tissue.

According to another embodiment of the present invention, the surface of the deposition part preferably has an arithmetic average roughness Ra of 1.0 µm or more.

This provides a device for cryopreservation that enables easier release and recovery of a cell or tissue during thawing. The arithmetic average roughness Ra is a value determined by extracting a reference length of a section of a measured roughness curve and averaging the roughness in the extracted section. In the present invention, the arithmetic average roughness Ra can be measured using a stylus type surface roughness tester, with a cut-off value of 0.8 mm and a reference length of 4.0 mm. A preferred upper limit of the arithmetic average roughness Ra is 10 µm or less. The arithmetic average roughness Ra of the surface of the deposition part is more preferably 1.0 to 5 µm, still more preferably 1.5 to 3.5 µm. When the surface of the deposition part has an arithmetic average roughness Ra in the above range, the effects of the present invention can be more sufficiently exerted.

In the device for cryopreservation of the present invention, the protrusion for holding a cell or tissue and the recess for holding a preservation solution may be arranged in a regular and uniform pattern or in an irregular and non-uniform (i.e., random) pattern. In the device for cryopreservation of the present invention, the surface configuration including the protrusion for holding a cell or tissue and the recess for holding a preservation solution can have any desired pattern such as a pillar, block, striped, hole, or conical pattern.

The deposition part of the device for cryopreservation of the present invention may be made of a non-absorbing material that does not absorb a preservation solution or may have a preservation solution absorber that absorbs a preservation solution.

First, the following describes a case where the deposition part of the device for cryopreservation of the present invention on which a cell or tissue is to be deposited is made of a non-absorbing material.

In the device for cryopreservation of the present invention, when the deposition part on which a cell or tissue is to be deposited is a non-absorbing material, examples of the non-absorbing material include various resins including polyester resins such as polyethylene terephthalate (PET) and polyethylene naphthalate (PEN), acrylic resin, epoxy resin, silicone resin, polycarbonate resin, diacetate resin, triacetate resin, polyarylate resin, polyvinyl chloride resin, polysulfone resin, polyether sulfone resin, polyimide resin, polyamide resin, polyolefin resin, cyclic polyolefin resin, and fluorine resins such as polytetrafluoroethylene (PTFE); various metals such as aluminum, aluminum alloy, gold, gold alloy, silver, silver alloy, iron, copper, copper alloy, and stainless steel; glass; and rubber.

Next, the following describes a method of forming the protrusion for holding a cell or tissue and the recess for storing a preservation solution on the deposition part for a cell or tissue of the device for cryopreservation of the present invention.

The protrusion for holding a cell or tissue and the recess for storing a preservation solution can be formed on the surface of the deposition part of the device for cryopreservation of the present invention by various methods according to materials. Specifically, when resin such as PET is used as a material of the deposition part, a protrusion and a recess of desired shapes can be formed on the surface of the deposition part by a method such as cutting, surface polishing, or molding by pressing a heated mold. When a metal is used as a material of the deposition part, a protrusion and a recess of desired shapes can be formed on the surface of the deposition part by a method such as cutting, surface polishing, or shot peening. When glass is used as a material of the deposition part, a protrusion and a recess of desired shapes can be formed on the surface of the deposition part by a method such as etching or fine polishing.

Next, the following describes a case where the deposition part of the device for cryopreservation of the present invention has a preservation solution absorber.

When the deposition part for a cell or tissue of the device for cryopreservation of the present invention has a preservation solution absorber, advantageously, an excess preservation solution around a cell or tissue can be removed, and the impact of chemical toxicity of a cryoprotectant can be reduced. When the deposition part for a cell or tissue has a preservation solution absorber, it eliminates the need for the step of removing an excess vitrification solution, which is a step required particularly in the vitrification cryopreservation method, and the deposited cell or tissue is surrounded by a very small amount of the preservation solution, so that an improved viability of the cell or tissue is expected.

When the deposition part for a cell or tissue in the device for cryopreservation of the present invention has a preservation solution absorber, the preservation solution absorber may be selected from a porous fibrous structure, a porous resin structure, a porous metal structure, and a porous metal oxide structure. The "porous" herein means that the absorber is a structure having pores on the surface thereof. The absorber is more preferably a structure having pores on the surface of and inside the absorber. The preservation solution absorber (any of the above porous structures) preferably has a thickness of 10 μm to 5 mm, more preferably 20 μm to 2.5 mm. When the preservation solution absorber is a thin sheet, the non-absorbing material described above as an enforcement member can be used together as a support.

In the present invention, the porous fibrous structure to be used as the preservation solution absorber may be paper or nonwoven fabric, for example. The paper preferably satisfies that the proportion of binding agent components such as a binder in the whole paper is 10 mass % or less, more preferably 5 mass % or less, still more preferably 3 mass % or less. This leads to excellent preservation solution absorbency. The proportion of papermaking chemicals contained in the paper in the whole paper is preferably 1 mass % or less. Chemicals such as fluorescent brighteners, dyes, and cationic sizing agents among papermaking chemicals usually contained in paper may disadvantageously affect cells.

When the fibrous porous structure is paper, it preferably has a density of 0.1 to 0.6 g/cm$^3$ and a grammage of 10 to 130 g/m$^2$. The paper preferably has a density of 0.12 to 0.3 g/cm$^3$ and a grammage of 10 to 100 g/m$^2$ in order to provide a device for cryopreservation having excellent preservation solution absorbency as well as providing such an excellent visibility of a cell or tissue that the cell or tissue deposited on the deposition part can be observed under a transmission microscope.

When the fibrous porous structure is nonwoven fabric, examples of the fiber contained in the nonwoven fabric include cellulose fiber, rayon and cupro fiber which are regenerated fibers made of cellulose fiber, acetate fiber which is a semi-synthetic fiber made of cellulose fiber, polyester fiber, nylon fiber, acrylic fiber, polypropylene fiber, polyethylene fiber, polyvinyl chloride fiber, vinylidene fiber, polyurethane fiber, vinylon fiber, glass fiber, and silk fiber. Nonwoven fabric made by mixing fibers among these fibers may also be used. Preferred are cellulose fiber, rayon and cupro fiber which are cellulose regenerated fibers made of cellulose fiber, as well as acetate fiber which is a semi-synthetic fiber derived from cellulose fiber.

When the fibrous porous structure is nonwoven fabric, it preferably has a density of 0.1 to 0.4 g/cm$^3$ and a grammage of 10 to 130 g/m$^2$. In order to provide a device for cryopreservation having excellent preservation solution absorbency as well as providing excellent visibility of a cell or tissue, the nonwoven fabric preferably has a density of 0.12 to 0.3 g/cm$^3$ and a grammage of 10 to 100 g/m$^2$.

Similar to the case of paper as mentioned above, nonwoven fabric to be used as the preservation solution absorber also preferably satisfies that the proportion of binding agent components such as a binder in the whole nonwoven fabric is 10 mass % or less, more preferably 5 mass % or less, still more preferably 3 mass % or less. The nonwoven fabric is preferably free from a binding agent.

Unlike paper, nonwoven fabric may be produced by various methods. The nonwoven fabric with a reduced proportion of binding agent components is preferably produced by spun-bonding or melt-blowing, and preferably produced by aligning fibers by a wet process or a dry process, and then performing hydroentanglement or needle punching. As mentioned above, the fiber contained in the nonwoven fabric in the present invention is preferably cellulose fiber, rayon or cupro fiber which is a cellulose regenerated fiber derived from cellulose fiber, or acetate fiber which is a semi-synthetic fiber made of cellulose fiber. When the nonwoven fabric is produced using such a fiber, the production method is preferably hydroentanglement or needle punching regardless of whether the fibers are aligned by a wet process or a dry process.

Examples of the porous resin structure to be used as the preservation solution absorber in the present invention include porous structures having a porous structure which is formed of a microfibrous structure prepared by at least uniaxially stretching a resin material and heating the resin material up to a temperature of not lower than the melting point of the resin to sinter the resin material, as disclosed in JP S42-13560 B and JP H08-283447 A; and a porous structure having a porous structure which is formed by putting solid powder of thermoplastic resin prepared by, for example, emulsion polymerization or pulverization into a mold, heating and sintering the powdery particles to fuse the surfaces of the particles, and then cooling the particles, as disclosed in JP 2009-235417 A. Use of a porous structure as the preservation solution absorber is preferred because it enables production of a device for cryopreservation having excellent preservation solution absorbency as well as providing excellent visibility of a cell or tissue.

Examples of the resin constituting the porous resin structure (porous resin sheet) include polyethylene species such as low-density polyethylene, high-density polyethylene, and ultra-high molecular weight polyethylene, polypropylene, polymethyl methacrylate, polystyrene, fluororesins such as polytetrafluoroethylene and polyvinylidene difluoride, ethylene-vinyl acetate copolymers, polyamide, styrene-acrylonitrile copolymers, styrene-butadiene-acrylonitrile terpolymers, polycarbonate, and polyvinyl chloride. In particular, a porous resin sheet containing a fluororesin such as polytetrafluoroethylene or polyvinylidene difluoride significantly improves the visibility of a cell or tissue under a transmission microscope when the cell or tissue is deposited on the deposition part together with a preservation solution, advantageously making it possible to provide a device for cryopreservation particularly excellent in the visibility of a cell or tissue. The porous resin sheet may be a membrane filter for filtering which is commercially available for the purposes of physical and chemical experiments and researches.

In the present invention, the porous metal structure to be used as the preservation solution absorber may be a porous metal sheet made of a metal such as copper, copper alloy, aluminum, aluminum alloy, gold, gold alloy, silver, silver alloy, tin, zinc, lead, titanium, nickel, or stainless steel. The porous metal oxide structure may be preferably a porous metal oxide structure made of a metal oxide such as silica, alumina, zirconium, or quartz glass. The porous metal structure and the porous metal oxide structure may be porous structures respectively containing two or more of the metals and two or more of the metal oxides. The porous metal oxide structure is preferred because it enables production of a device for cryopreservation providing excellent visibility of a cell or tissue under a transmission microscope.

In the present invention, the porous metal structure and the porous metal oxide structure to be used as the preservation solution absorbers can be produced by a commonly known method. The porous metal structure to be used as the preservation solution absorber can be produced by powder metallurgy or the spacer method, for example. Also, what is called the powder space holder method, which is a combination of resin injection molding and powder metallurgy, can be preferably used. For example, methods disclosed in WO 2006/041118 and JP 4578062 B can be used. Specifically, metal power and a resin serving as a spacer are mixed, and then the mixture is pressure-molded and fired in a high-temperature environment so that the metal powder is sintered and the resin serving as a spacer is evaporated. Thereby, a porous metal sheet is obtained. In the case of the powder space holder method, for example, a resin binder may also be mixed with the metal powder and the resin serving as a spacer. Alternatively, other methods of producing metal porous bodies, such as melt foaming and gas expansion, can be used in which metal powder is heated at high temperature and gas is injected to form voids. Methods of producing metal porous bodies using a foaming agent, such as slurry foaming, can also be used. The porous metal oxide structure to be used as the preservation solution absorber can be produced by, for example, methods disclosed in JP 2009-29692 A and JP 2002-160930 A.

When the preservation solution absorber is a porous body selected from the porous resin structures, porous metal structures, and porous metal oxide structures described above, the porous body preferably has a pore size of 0.02 to 50 μm, more preferably 0.05 to 25 μm. When the pore size is smaller than 0.02 μm, the preservation solution may not be sufficiently absorbed when the preservation solution is dropped. Further, such a porous structure may be difficult to produce. When the pore size is greater than 50 μm, it may be difficult to form the protrusion for holding a cell or tissue and the recess for storing a preservation solution on the deposition part of the device for cryopreservation of the present invention. When the pore size is greater than 25 μm, the visibility of a cell or tissue may be reduced under a transmission microscope. In the case of a porous resin structure, the pore size of the porous body corresponds to the diameter of the largest pore measured by the bubble point test. In the case of a porous metal structure or a porous metal oxide structure, the pore size corresponds to the average pore diameter determined by image observation of the surface and cross section of the porous body.

The preservation solution absorber preferably has a porosity of 20 vol % or more, more preferably 30 vol % or more. When the preservation solution absorber is a porous body such as the porous resin structure, the porous metal structure, or the porous metal oxide structure, the pores inside the porous body are preferably continuous not only in the thickness direction but also in the direction perpendicular to the thickness direction. Such a configuration enables effective use of the pores inside the porous body, leading to good performance of absorbing the preservation solution. The thickness of the preservation solution absorber and the porosity of the porous body may be appropriately selected in accordance with factors such as the type of a cell or tissue used and the amount of the preservation solution to be dropped with the cell or tissue.

The porosity is defined by the following formula. The void volume V can be determined as the value per unit area (m$^2$) by multiplying the cumulative pore volume (mL/g) by the dry solids content (g/m$^2$) of the preservation solution absorber. The cumulative pore volume is the total volume of pores having a pore radius of 3 nm to 400 nm in the preservation solution absorber and is determined by measurement and data processing with a mercury porosimeter (name: Autopore II 9220, Micromeritics Instrument Corporation). The thickness T of the preservation solution absorber can be measured on a photograph of the cross section of the preservation solution absorber taken with an electron microscope.

$$P=(V/T)\times100(\%)$$

P: porosity (%)
V: void volume (ml/m$^2$)
T: thickness (μm)

In the device for cryopreservation of the present invention, when the deposition part on which a cell or tissue is to be deposited has a preservation solution absorber, the protrusion for holding a cell or tissue and the recess for storing a preservation solution can be formed by various methods according to the material, as described above. Specifically, when the preservation solution absorber is a porous fibrous structure or a porous resin structure made of polytetrafluoroethylene or the like, a protrusion and a recess of desired shapes can be formed on a surface of the preservation solution absorber to be used in the deposition part by a method such as molding by pressing a heated mold. When the preservation solution absorber is a porous metal structure, a protrusion and a recess of desired shapes can be formed on a surface of the preservation solution absorber by a method such as etching, shot peening, or surface polishing. When the preservation solution absorber has pores, preferably, a protrusion and a recess of desired shapes are formed on the surface of the preservation solution absorber without blocking the pores in the preservation solution absorber. The deposition part having a preservation solution absorber is preferably one in which a protrusion and a recess on the surface of the preservation solution absorber serve as the protrusion and the recess on the surface of the deposition part.

The height of the protrusion formed on the deposition part by the method described above can be determined by profilometry using a confocal microscope. Examples of other methods of determining the height of the protrusion formed on the deposition part include a method in which the height is analyzed using depth synthesis function of a digital microscope "VHX-500" available from Keyence Corporation, a method in which the height is analyzed using a profilometer "VK-X1000" available from Keyence Corporation, and a method in which a cross section of the deposition part is observed using an electronic microscope. The pattern pitch between the protrusions described above can also be determined in a similar manner.

In the present invention, when the deposition part has the non-absorbing material as an enforcement member in addition to the preservation solution absorber, an adhesive layer may be formed between the preservation solution absorber and the non-absorbing material. The adhesive layer may contain an adhesive composition such as an instant adhesive composition typified by a moisture-curable adhesive substance, a hot-melt adhesive composition, or a photo-curable adhesive composition. Preferred examples thereof include compositions containing any of water-soluble polymeric compounds such as polyvinyl alcohol, hydroxycellulose, polyvinyl pyrrolidone, and starch paste; and water-insoluble resins such as vinyl acetate resin, acrylic resin, epoxy resin, urethane resin, elastomeric resin, cyanoacrylate resin, fluorine resin, silicone resin, nitrocellulose resin, nitrile rubber resin, styrene-butadiene resin, urea resin, styrene resin, phenolic resin, polyimide resin, polyamide resin, polyester resin, bismaleimide resin, olefinic resin, and EVA resin. The adhesive layer may contain one resin or may contain multiple resins. The adhesive layer preferably has a solids content of 0.01 to 100 g/m$^2$, more preferably 0.1 to 50 g/m$^2$.

The area of the deposition part of the device for cryopreservation of the present invention may be appropriately determined in accordance with factors such as the amount of the preservation solution to be dropped with the cell or tissue, and may be any value. For example, the area thereof is preferably 1 mm$^2$ or larger, more preferably 2 to 400 mm$^2$ per microliter of the preservation solution to be dropped. When the deposition part in one device for cryopreservation has multiple preservation solution absorbers on the non-absorbing support, one continuous preservation solution absorber portion preferably has the above area.

Preferably, the deposition part of the device for cryopreservation of the present invention on which a cell or tissue is to be deposited includes a soluble layer containing a water-soluble polymeric compound on an outermost surface of the deposition part. As described above, the device for cryopreservation of the present invention is used in the following manner. In the freezing procedure, a cell or tissue is deposited together with a preservation solution on the deposition part of the device for cryopreservation, and then immersed and frozen in a coolant (e.g., liquid nitrogen). In thawing, the frozen cell or tissue is taken out together with the device for cryopreservation and immersed and thawed in a thawing solution. When the soluble layer is present on the outermost surface of the deposition part, the soluble layer entirely or partially dissolves in the thawing solution during thawing of the cell or tissue, which synergistically improves cell or tissue releasability, with the combined effect of the protrusion and recess of desired shapes formed on the deposition part.

In the present invention, examples of the water-soluble polymeric compound contained in the soluble layer include cellulose derivatives such as hydroxyethylcellulose, hydroxypropylcellulose, and carboxymethylcellulose, starch and derivatives thereof, gelatin, casein, alginic acid and salts thereof, polyvinyl alcohol, polyvinylpyrrolidone, styrene-maleic acid copolymer salts, and styrene-acrylic acid copolymer salts. Preferred among these are alginic acid and salts thereof and gelatin because they are soluble in the preservation solution and has an appropriate film formation effect. Particularly preferred is polyvinyl alcohol because it is a non-biological material and less toxic to a cell or tissue. These water-soluble polymeric compounds may be used alone or in combination of two or more thereof. The soluble layer may contain a cross-linking agent in the range that does not reduce the solubility of the soluble layer in the thawing solution to below 10 mass %.

In the present invention, when the deposition part has the preservation solution absorber, preferably, the deposition part preferably includes a protrusion and a recess of desired shapes without blocking the pores of the preservation solution absorber. The soluble layer may be provided on the preservation solution absorber as long as the absorbency of the preservation solution absorber is not significantly reduced.

In the present invention, when the device for cryopreservation includes the soluble layer on the preservation solution absorber, a greater solids content of the soluble layer leads to narrower pores in the preservation solution absorber, and thus tends to lead to a lower preservation solution absorbency. In contrast, the cell or tissue releasability in the thawing procedure improves as the solids content of the soluble layer increases. For this reason, the water-soluble polymeric compound contained in the soluble layer preferably has a solids content of 0.01 to 100 $g/m^2$, more preferably 0.1 to 10 $g/m^2$.

In long-term cryopreservation of a cell or tissue using the device for cryopreservation of a cell or tissue of the present invention, the cell or tissue may be covered with a cap or the device for cryopreservation may be sealed in a container in any form to be isolated from the outside environment. A cell or tissue frozen by direct contact with non-sterile liquid nitrogen is not always guaranteed to be in a sterilized condition even if the device for cryopreservation is sterilized. Thus, the deposition part holding a cell or tissue is occasionally covered with a cap, or the device for cryopreservation is sealed in a container before freezing so as not to cause direct contact of a cell or tissue with liquid nitrogen. Such a freezing method without direct contact with liquid nitrogen is the mainstream in developed countries such as European countries. In addition, also when freezing a cell or tissue by direct contact with liquid nitrogen, the deposition part may be covered with a cap in order to protect the cell or tissue deposited on the device for cryopreservation from a physical shock or the like in a liquid nitrogen tank where the cell or tissue is stored. For this reason, the cap and the container are preferably made of any of liquid nitrogen-resistant material such as various metals, various resins, glass, and ceramics. They may have any shape as long as they are not brought into contact with the deposition part and can shield a cell or tissue from the outside environment. The cap may have any shape, such as a half-spindle-shaped or dome-shaped cap like a cap for pencils, or a cylindrical straw cap. The container may be any one capable of including or storing the device for cryopreservation to seal it without contact with the cell or tissue deposited and may have any shape.

In the present invention, the device for cryopreservation may be used in combination with such a cap or container capable of shielding a cell or tissue on the deposition part from the outside environment as long as the effects of the present invention are not impaired. The device for cryopreservation used in combination with such a cap or container is also included in the present invention.

The device for cryopreservation of the present invention may be preferably used in the Cryotop method, for example. The conventional Cryotop method is commonly used for cryopreservation of an embryo or egg, and is usually used for storage of a single cell or a small number of cells (e.g., less than 10 cells). In contrast, the device for cryopreservation of the present invention can also be suitably used for storage of a larger number of cells (e.g., storage of 10 to 1000000 cells). It can also be suitably used for storage of sheet-like cells (what is called cell sheets) formed from multiple cells. The use of the device for cryopreservation of the present invention allows a cell or tissue to be reliably held and cryopreserved with a small amount of a preservation solution surrounding the deposited cell or tissue in the cryopreservation procedure. Also, the cell or tissue can be easily released and recovered during thawing from the frozen state. Additionally, when the deposition part has the preservation solution absorber, not only the above effect can be achieved, but also an excess preservation solution surrounding the cell or tissue is absorbed in freezing the cell or tissue. Thus, the cell or tissue is less susceptible to damage from the preservation solution outside the cell during thawing or freezing, and can be cryopreserved with excellent viability.

Any method may be used for cryopreserving a cell or tissue using the device for cryopreservation of the present invention. For example, first, a cell or tissue immersed in a preservation solution is dropped onto the deposition part together with the preservation solution. An excess preservation solution surrounding the cell or tissue is removed with a pipette or the like as much as possible, as needed. When the deposition part of the device for cryopreservation has a preservation solution absorber, this procedure is unnecessary as the excess preservation solution is automatically removed. Next, the device for cryopreservation with the cell or tissue held on the deposition part is immersed in liquid nitrogen or the like to freeze the cell or tissue. The cap described above capable of shielding the cell or tissue on the deposition part from the outside environment may be attached to the deposition part, or the device for cryopreservation may be sealed into the container described above before the device is immersed in liquid nitrogen or the like. The preservation solution may be one usually used for freezing cells, such as eggs and embryos. For example, the preservation solution may be the aforementioned preservation solution prepared by adding a cryoprotectant (e.g., glycerol or ethylene glycol) to a physiological solution such as a phosphate buffered saline, or a preservation solution containing a large amount (at least 10 mass % or more, more preferably 20 mass % or more relative to the total mass of the preservation solution) of a cryoprotectant such as glycerol, ethylene glycol, or dimethyl sulfoxide (DMSO). In the thawing procedure, the device for cryopreservation is taken out from the coolant such as liquid nitrogen and the deposition part holding the frozen cell or tissue is immersed in a thawing solution. The cell or tissue is then recovered.

Examples of the cell that can be cryopreserved using the device for cryopreservation of the present invention include reproductive cells such as eggs, embryos, and sperms from mammals (for example, human, bovine, swine, equine, leporine, rat, and mouse); and pluripotent stem cells such as induced pluripotent stem cells (iPS cells) and embryonic stem cells (ES cells). Also included are culture cells such as primary culture cells, subculture cells, and cell lines. In one or more embodiments, examples of the cell include adhesive cells such as fibroblasts, cancer-derived cells (e.g., pancreatic cancer cells and hepatoma cells), epithelial cells, vascular endothelial cells, lymphatic endothelial cells, neuronal cells, chondrocytes, tissue stem cells, and immune cells. Examples of the tissue that can be cryopreserved include tissues formed of homologous cells and tissues formed of heterologous cells, such as tissues of ovary, skin, corneal epithelium, periodontal ligament, and myocardium. The present invention is particularly suitable for cryopreservation of sheet-like tissues (e.g., cell sheets and skin tissues). The device for cryopreservation of the present invention can be suitably used for cryopreservation of not only native tissues harvested from living bodies but also artificial tissues, such as cultured skins obtained by in vitro growth of cells, what is called cell sheets formed in vitro, and a three-dimensional tissue model described in JP 2012-205516 A. The device for cryopreservation of the present invention is suitably used as a device for cryopreservation of the aforementioned cells or tissues.

The deposition part of the device for cryopreservation of the present invention has been described above. The device for cryopreservation of the present invention may include a handle together with the deposition part. The presence of the handle advantageously leads to good working efficiency in the cryopreservation and thawing procedures.

FIG. 1 is an overall view showing an exemplary device for cryopreservation of a cell or tissue of the present invention. In FIG. 1, a device for cryopreservation 9a includes a handle 1, a flat sheet-like support 2, and a flat sheet-like deposition part 3 formed on the support 2.

The handle 1 is preferably made of a liquid nitrogen-resistant material. Preferred examples of such a material include various metals such as aluminum, iron, copper, and stainless steel alloy, ABS resin, polypropylene resin, polyethylene resin, fluorine resin, various engineering plastics, and glass. In FIG. 1, the handle 1 has a cylindrical shape, but the handle may have any shape. As described later, in some cases, a cap may be placed on the deposition part 3 so as to avoid direct contact between a cell or tissue and liquid nitrogen or to protect a cell or tissue. In this case, the handle 1 may be tapered such that the diameter of the cylinder continually decreases from the side with no deposition part 3 to the side with the deposition part 3, thereby improving the working efficiency when placing a cap.

The following describes a method for connecting the handle 1 and the support 2 shown in FIG. 1. When the handle 1 is made of resin, the support 2 can be connected to the handle 1 by insert molding during molding, for example. Alternatively, the support 2 can be connected to the handle 1 using an adhesive by forming a structure-inserting part (not shown) in the handle 1. Various adhesives may be used, and preferred are silicone or fluorine adhesives which are resistant to low temperatures.

Figure 2:
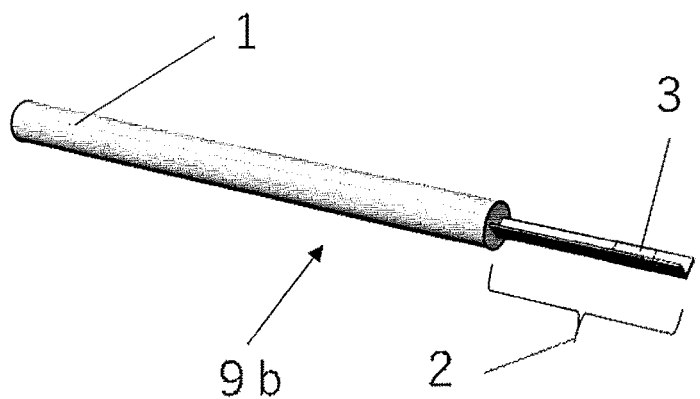
FIG. 2 is an overall view showing another exemplary device for cryopreservation of a cell or tissue of the present invention.

FIG. 2 is an overall view showing another exemplary device for cryopreservation of a cell or tissue of the present invention. In FIG. 2, a device for cryopreservation 9b includes the handle 1, the V-shaped sheet-like support 2, and the V-shaped sheet-like deposition part 3 formed on the support 2. Dropwise attachment of a cell or tissue and a preservation solution to the center of the V-shaped sheet-like deposition part can improve the working efficiency when removing an excess preservation solution with a pipette or the like.

Figure 3:
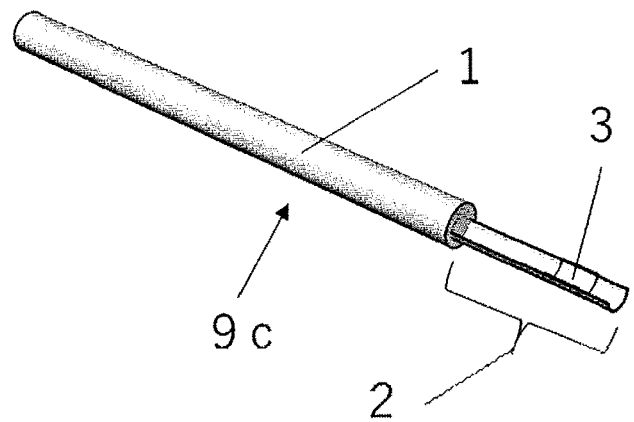
FIG. 3 is an overall view showing still another exemplary device for cryopreservation of a cell or tissue of the present invention.

FIG. 3 is an overall view showing still another exemplary device for cryopreservation of a cell or tissue of the present invention. In FIG. 3, a device for cryopreservation 9c includes the handle 1, the curved sheet-like support 2, and the curved sheet-like deposition part 3 formed on the support 2. As is the case with the device for cryopreservation shown in FIG. 2, dropwise attachment of a cell or tissue and a preservation solution to the center of the curved sheet-like deposition part can improve the working efficiency when removing an excess preservation solution with a pipette or the like.

Figure 4:
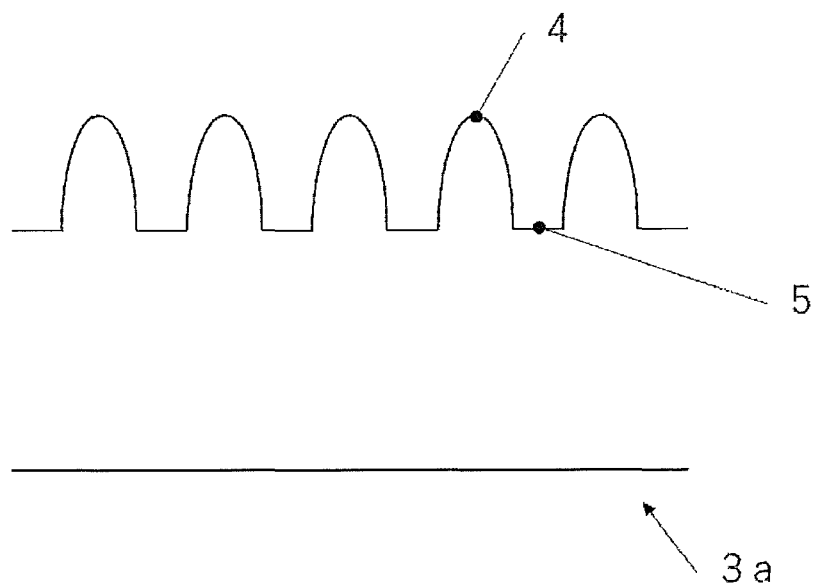
FIG. 4 is a schematic cross-sectional structure view showing an exemplary deposition part of the device for cryopreservation of a cell or tissue of the present invention.

FIG. 4 is a schematic cross-sectional structure view showing an exemplary deposition part of the device for cryopreservation of a cell or tissue of the present invention. A deposition part 3a in FIG. 4 includes protrusions 4 for holding a cell or tissue and recesses 5 for storing a preservation solution.

Figure 5:
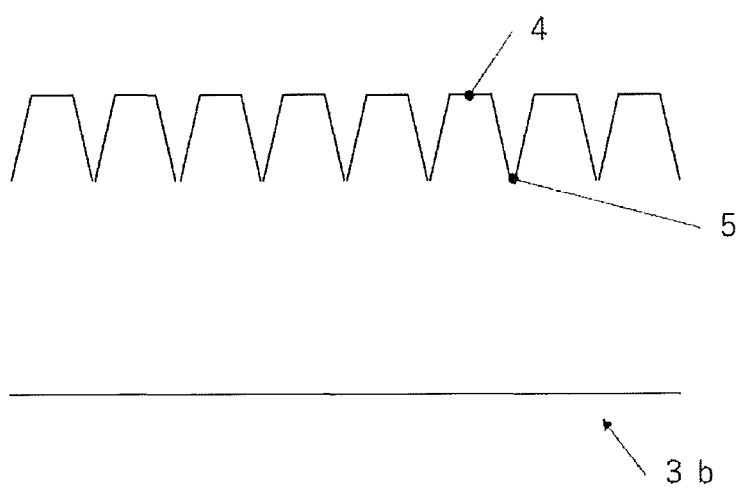
FIG. 5 is a schematic cross-sectional structure view showing another exemplary deposition part of the device for cryopreservation of a cell or tissue of the present invention.

FIG. 5 is a schematic cross-sectional structure view showing another exemplary deposition part of the device for cryopreservation of a cell or tissue of the present invention. A deposition part 3b in FIG. 5 includes the flat-topped protrusions 4 for holding a cell or tissue and the recesses 5 for storing a preservation solution. In such a configuration, a cell or tissue deposited has a larger contact area with the protrusions 4 and thus can be more reliably held.

Figure 6:
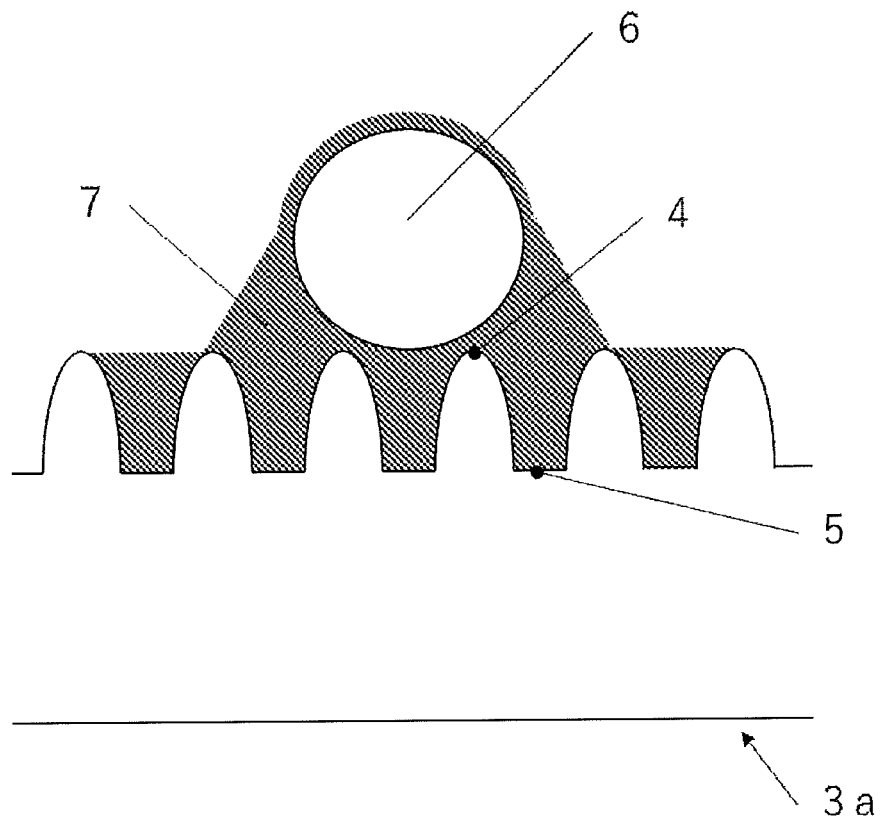
FIG. 6 is a model view showing a cell and a preservation solution attached dropwise to the deposition part shown in FIG. 4.

FIG. 6 is a model view showing a cell and a preservation solution attached dropwise to the deposition part shown in FIG. 4. In FIG. 6, the deposition part 3a includes the protrusions 4 for holing a cell or tissue and the recesses 5 for storing a preservation solution. A cell 6 shown in FIG. 6 is deposited together with a preservation solution 7 on the deposition part 3a. Here, the cell 6 is surrounded by the preservation solution 7, and is reliably held by the protrusions 4 via the preservation solution 7. A small amount of the preservation solution 7 stays around the cell 6, and the remaining excess amount of a vitrification solution is stored in the recesses 5.

Figure 7:
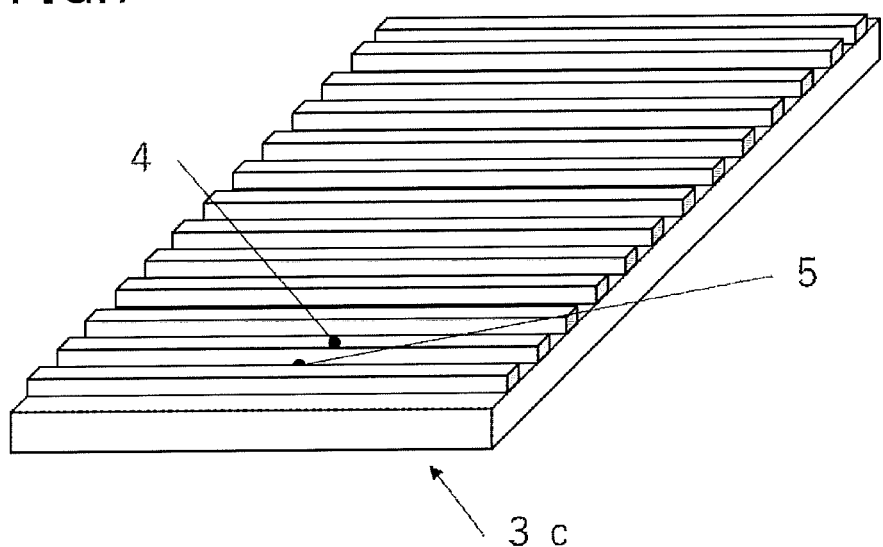
FIG. 7 is a perspective view showing an exemplary deposition part of the device for cryopreservation of a cell or tissue of the present invention.

FIG. 7 is a perspective view showing an exemplary deposition part of the device for cryopreservation of a cell or tissue of the present invention. A deposition part 3c shown in FIG. 7 includes the flat-topped protrusions 4 for holding a cell or tissue and the recesses 5 for storing a preservation solution. The deposition part as a whole has a line-and-space-shaped (stripe shaped), uniform pattern.

Figure 8:
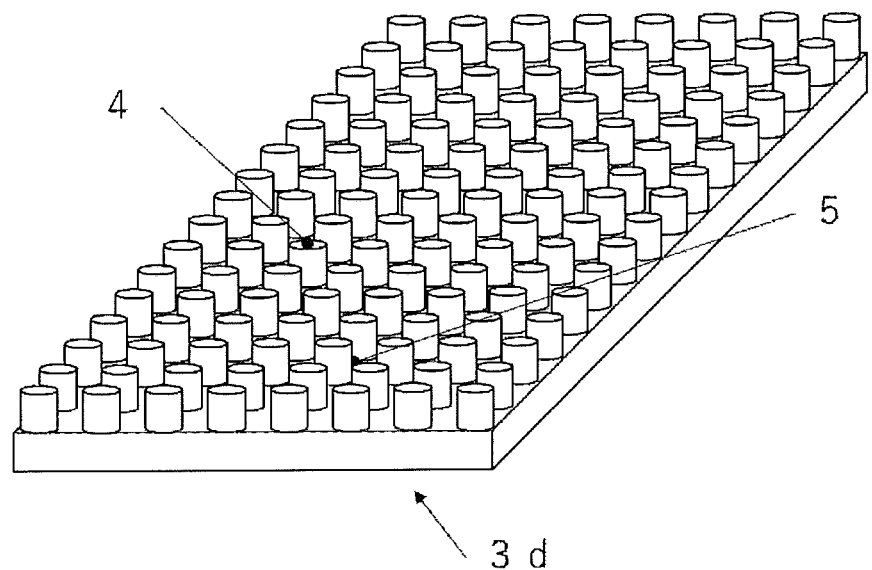
FIG. 8 is a perspective view showing another exemplary deposition part of the device for cryopreservation of a cell or tissue of the present invention.

FIG. 8 is a perspective view showing another exemplary deposition part of the device for cryopreservation of a cell or tissue of the present invention. A deposition part 3d shown in FIG. 8 as a whole has a uniform pattern of cylindrical (pillar-shaped) structures. The deposition part 3d includes the flat-topped the protrusions 4 for holding a cell or tissues and the recesses 5 for storing a preservation solution. The recesses 5 are connected with each other in the deposition part as a whole, and can store a larger amount of an excess preservation solution. Thus, in the freezing procedure, the deposition part can be suitably used for dropwise attachment of a larger amount of a preservation solution when a cell or tissue is attached dropwise to the deposition part.

Figure 9:
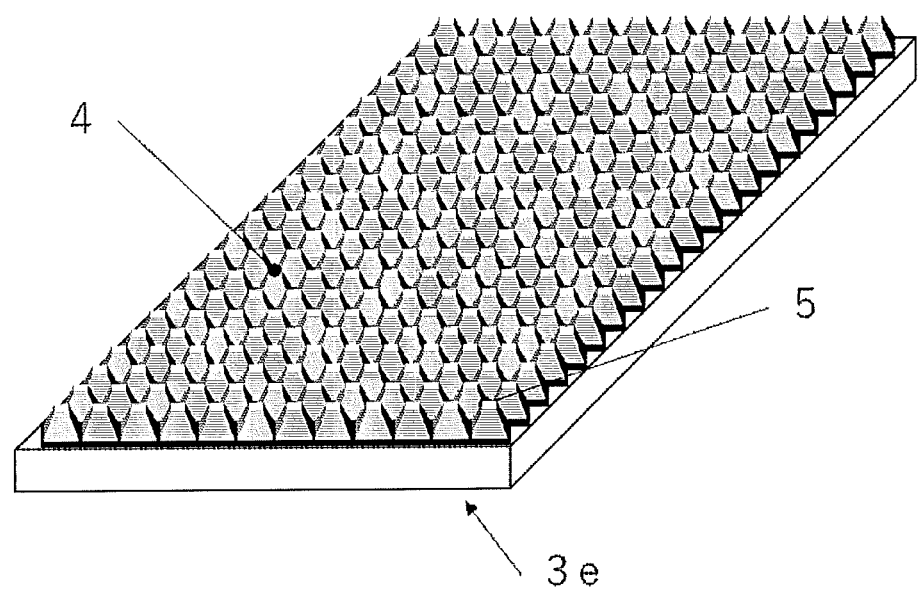
FIG. 9 is a perspective view showing still another exemplary deposition part of the device for cryopreservation of a cell or tissue of the present invention.

FIG. 9 is a perspective view showing still another exemplary deposition part of the device for cryopreservation of a cell or tissue of the present invention. A deposition part 3e shown in FIG. 9 as a whole has a uniform pattern of substantially four-sided pyramid-shaped structures each having a top portion, on the upper surface (a side on which a cell or tissue is to be deposited) of the deposition part as a whole. The deposition part 3e includes the substantially four-sided pyramid-shaped protrusions 4 and the recesses 5 for storing a preservation solution. Since each protrusion has a smaller contact area with a cell or tissue, a frozen cell or tissue can be easily released and recovered during thawing.

Figure 10:
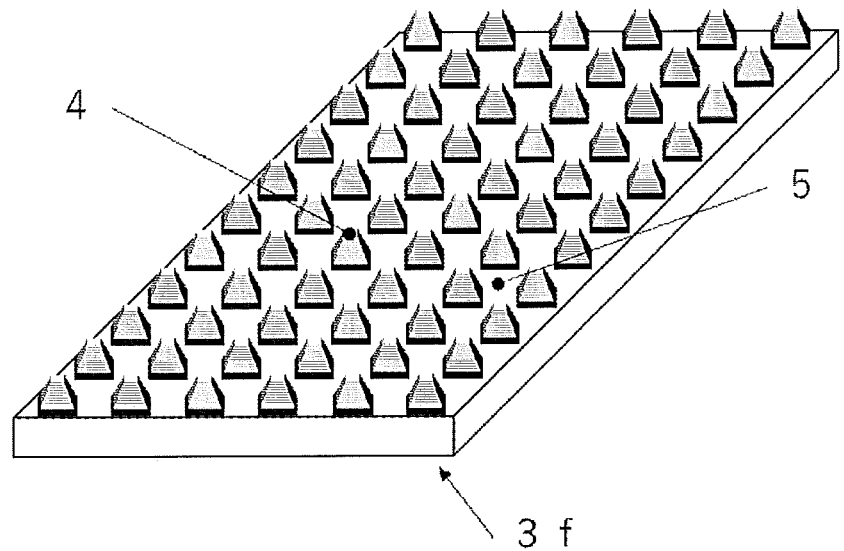
FIG. 10 is a perspective view showing still another exemplary deposition part of the device for cryopreservation of a cell or tissue of the present invention.

FIG. 10 is a perspective view showing still another exemplary deposition part of the device for cryopreservation of a cell or tissue of the present invention. Similar to FIG. 9, a deposition part 3f shown in FIG. 10 as a whole has a uniform pattern of substantially four-sided pyramid-shaped structures each having a top portion, on the upper surface (a side on which a cell or tissue is deposited) of the deposition part. The deposition part 3f has the substantially four-sided pyramid-shaped protrusions 4 and the recesses 5 for storing a preservation solution. The substantially four-sided pyramid-shaped structures are less dense in FIG. 10 than in FIG. 9. The deposition part having such a configuration can store a larger amount of a preservation solution in the recesses 5 than the one shown in FIG. 9. Thus, the deposition part can be suitably used for dropwise attachment of a larger amount of a preservation solution when a cell or tissue is attached dropwise to the deposition part in the freezing procedure.

Figure 11:
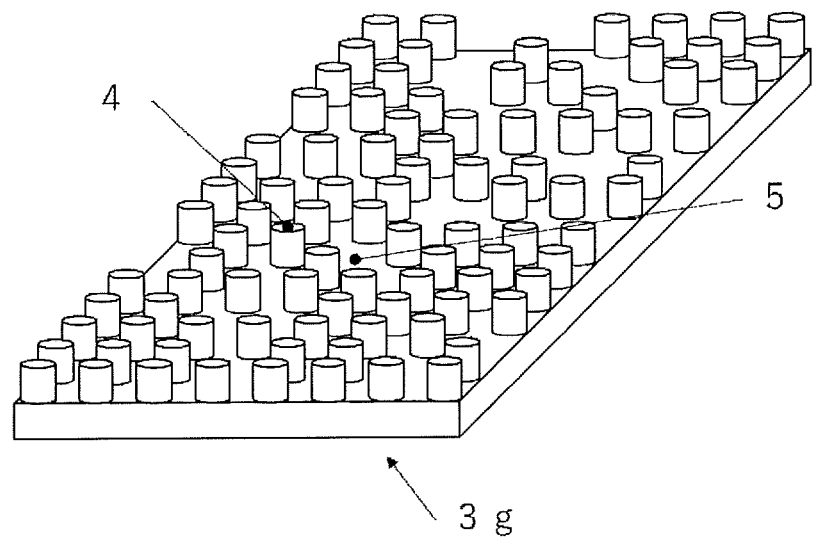
FIG. 11 is a perspective view showing still another exemplary deposition part of the device for cryopreservation of a cell or tissue of the present invention.

FIG. 11 is a perspective view showing still another exemplary deposition part of the device for cryopreservation of a cell or tissue of the present invention. A deposition part 3g shown in FIG. 11 includes cylindrical structures. The deposition part 3g includes the cylindrical protrusions 4 and the recesses 5 for storing a preservation solution. Such a deposition part with cylindrical structures is an example in which the deposition part has a non-uniform pattern (random pattern) in each region.

Figure 12:
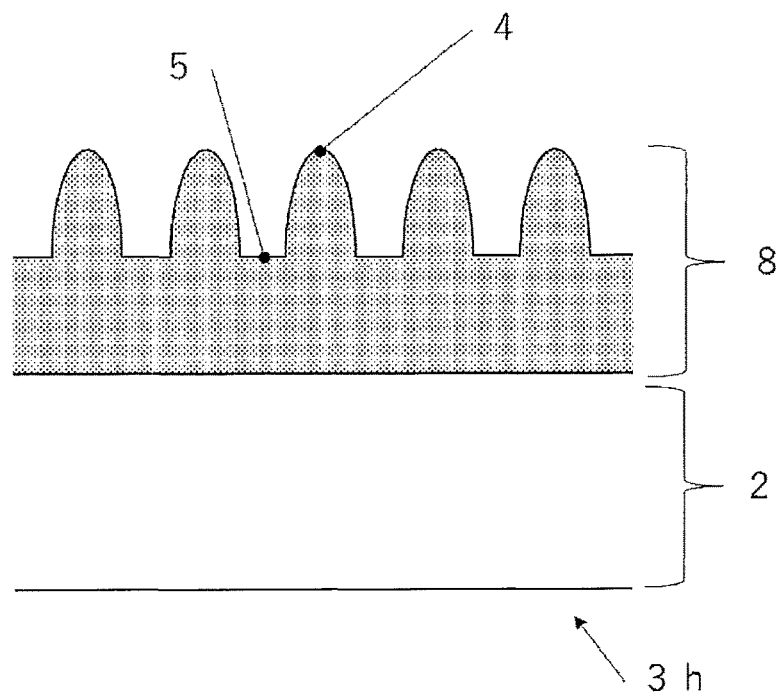
FIG. 12 is a cross-sectional structure view showing an exemplary deposition part in the case where the device for cryopreservation of a cell or tissue of the present invention has a preservation solution absorber.

FIG. 12 is a cross-sectional structure view showing an exemplary deposition part in the case where the device for cryopreservation of a cell or tissue of the present invention has a preservation solution absorber. In FIG. 12, a deposition part 3h has a preservation solution absorber 8 on the support 2. The preservation solution absorber 8 includes the protrusions 4 for holding a cell or tissue and the recesses 5 for storing a preservation solution. In the deposition part 3h, when a cell or tissue is attached dropwise together with a preservation solution in the freezing procedure, the protrusions 4 can reliably hold the cell or tissue, the recesses 5 stores the preservation solution, and the preservation solution absorber 8 removes an excess preservation solution surrounding the cell or tissue. This eliminates the need for removing an excess preservation solution using a pipette or the like, and enables quick vitrification.

Figure 13:
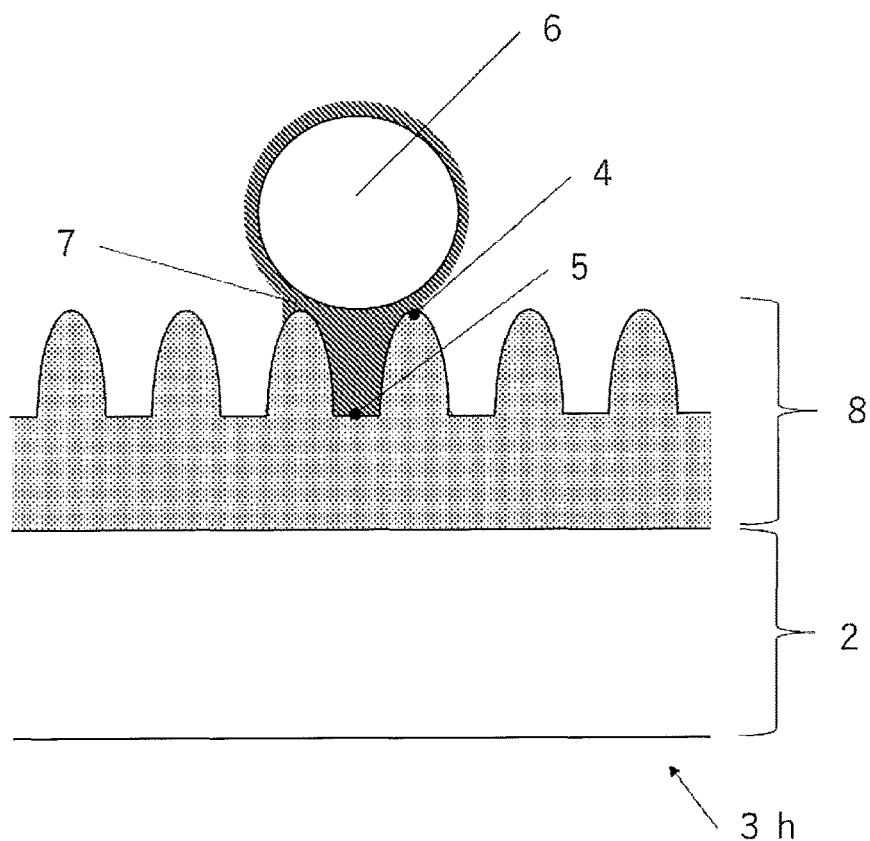
FIG. 13 is a model view showing a cell and a preservation solution attached dropwise to the deposition part shown in FIG. 12.

FIG. 13 is a model view showing a cell and a preservation solution deposited dropwise on the deposition part shown in FIG. 12. In FIG. 13, the preservation solution absorber 8 includes the protrusions 4 for holding a cell or tissue and the recesses 5 for storing a preservation solution. The cell 6 shown in FIG. 13 is deposited together with the preservation solution 7 on the preservation solution absorber 8. Here, the cell 6 is surrounded by the preservation solution 7, and is reliably held by the protrusions 4 via the preservation solution 7. A small amount of the preservation solution 7 required for vitrification stays around the cell 6, and the remaining excess amount of a preservation solution is stored in the recesses 5, but the preservation solution absorber 8 absorbs the excess preservation solution 7. This eliminates the need for removing an excess preservation solution using a pipette or the like, and enables quick vitrification, and further enables more reliable removal of an excess preservation solution.

EXAMPLES

The present invention is specifically described in more detail below with reference to examples. The present invention, however, should not be limited to the examples below.

In the examples, the height and pattern pitch of the protrusions formed on the deposition part were measured using a confocal microscope "Optelics® C130" available from Lasertec Corporation.

Example 1

A structure in which 5-μm tall four-sided pyramid-shaped structures having a pattern pitch of 50 μm were uniformly arranged was produced on a specific region of a transparent PET film as non-absorbing material by molding by pressing a heated mold using an embossing press machine, whereby a deposition part including protrusions for holding a cell or tissue and recesses for storing a preservation solution was obtained. The transparent PET film including a region of the produced deposition part was cut into a strip having a size of 1.5 mm×20 mm, and the strip was bonded to an ABS resin handle, whereby a device for cryopreservation of Example 1 was produced.

Example 2

A structure in which 1-μm tall hexagonal columns having a pattern pitch of 10 μm were uniformly arranged was produced on a specific region of a transparent PET film as non-absorbing material by molding by pressing a heated mold using an embossing press machine, whereby a deposition part including protrusions for holding a cell or tissue and recesses for storing a preservation solution was obtained. Subsequently, the transparent PET film was bonded to an ABS resin handle as in Example 1, whereby a device for cryopreservation of Example 2 was produced.

Example 3

Using porous polytetrafluoroethylene (pore size 0.2 μm, porosity 71%, thickness 35 μm) available from Advantec Toyo Kaisha, Ltd. as a preservation solution absorber, a structure in which 5-μm tall four-sided pyramid-shaped structures having a pattern pitch of 50 μm were uniformly arranged was produced on the preservation solution absorber by molding by pressing a heated mold, whereby a deposition part including protrusions for holding a cell or tissue and recesses for storing a preservation solution was obtained. Separately, onto a transparent PET film provided as a support was applied hot melt urethane resin "Purmelt® QR 170-7141P" available from Henkel Japan Ltd. as an adhesive layer to achieve a dry solids content of 30 g/m². Before the adhesive layer was completely solidified, a surface without surface structures of the preservation solution absorber subjected to molding by pressing a heated mold by the method described above was bonded to the support. Subsequently, the bonded product of the preservation solution absorber including a region of the produced deposition part and the support was cut into a strip having a size of 1.5 mm×20 mm, and the strip was bonded to an ABS resin handle, whereby a device for cryopreservation of Example 3 was produced.

Example 4

As in Example 3 described above, a bonded product of a preservation solution absorber having a structure including protrusions and recesses and a support was obtained. Subsequently, the bonded product was dip-coated with a 2 mass % aqueous solution of GOHSENX® WO-320R which is a polyvinyl alcohol having an ethylene oxide group (i.e., a water-soluble polymer), dried at room temperature, and then further dried by heat at 120° C. for 40 hours. The amount of the water-soluble polymer applied was 1.6 g/m². Subsequently, as in Example 1, the bonded product to which the water-soluble polymer was applied was cut into a strip having a size of 1.5 mm×20 mm, and the strip was bonded to an ABS resin handle, whereby a device for cryopreservation of Example 4 was produced.

Example 5

A device for cryopreservation of Example 5 was produced as in Example 4, except that a structure in which 1-μm tall four-sided pyramid-shaped structures having a pattern pitch of 50 μm were uniformly arranged was produced by molding by pressing a heated mold.

Comparative Example 1

A device for cryopreservation of Comparative Example 1 was produced as in Example 1, except that the transparent PET film as the non-absorbing material was not surface-treated.

Comparative Example 2

A device for cryopreservation of Comparative Example 2 was produced as in Example 3, except that the porous polytetrafluoroethylene was not surface-treated.

<Preparation of Spheres>

Spheres for use in cell or tissue releasability evaluation were prepared as follows. Mouse embryonic fibroblasts were cultured on a cell culture petri dish, and the fibroblasts were released and recovered by trypsin. Subsequently, the fibroblasts were seeded on a PrimeSurface® 96U plate available from Sumitomo Bakelite Co., Ltd. at a cell concentration of 50 cells/well, followed by suspension culture, whereby sphere formation was induced. After culturing for three days, spheres each having a diameter of about 100 μm were obtained.

<Freezing Procedure of Spheres and Evaluation of Operability During Freezing Procedure>

The spheres prepared by the method described above were recovered, and immersed in an equilibration solution (7.5 vol % dimethyl sulfoxide, 7.5 vol % ethylene glycol, 85 vol % 199 medium (Medium 199 available from GE Healthcare)). Subsequently, the spheres were recovered from the equilibration solution, and transferred to and immersed for 30 seconds in a vitrify preservation solution (a solution prepared by adding 15 vol % dimethyl sulfoxide, 15 vol % ethylene glycol, 14 vol % fetal bovine serum, and 0.5 M sucrose to the 199 medium serving as the base solution). Subsequently, the spheres were recovered together with a small amount of the vitrify preservation solution (about 0.4 μl) and deposited dropwise on the deposition parts of the devices for cryopreservation of Examples 1 to 5 and Comparative Example 1, using a stripper pipette (ORIGIO Japan). In each of the devices for cryopreservation of Examples 1 and 2 and Comparative Example 1 not having a preservation solution absorber, a single sphere was attached dropwise together with a small amount of the vitrify preservation solution to the deposition part. Subsequently, an excess vitrify preservation solution around the sphere was removed as much as possible using a stripper pipette under a transmission microscope. Then, the sphere on the deposition part was vitrified by being immersed in liquid nitrogen. In each of the devices for cryopreservation of Examples 3 to 5 and Comparative Example 2 having a preservation solution absorber, a single sphere was attached dropwise together with a small amount of the vitrify preservation solution to the deposition part. Subsequently, the state of an excess vitrify preservation solution being voluntarily absorbed was observed under a transmission microscope. When removal of an excess vitrification solution around the sphere was confirmed, the sphere on the deposition part was vitrified by being immersed in liquid nitrogen. The frozen device for cryopreservation was stored in a liquid nitrogen storage container until thawing.

The operability during the freezing procedure was as follows. In each of the device for cryopreservation of Examples 1 and 2 not having a preservation solution absorber, when attaching a sphere dropwise together with a small amount of a vitrify preservation solution to the deposition part, the vitrify preservation solution and the sphere were easily attached to the surface of the deposition part, enabling easy dropwise attachment of the sphere to the deposition part, as compared to Comparative Example 1. Also when removing an excess vitrify preservation solution, in the case of the devices for cryopreservation of Example 1 and Example 2, the vitrify preservation solution was stored in the recesses in the deposition part, and the vitrify preservation solution was easily attached to the surface of the deposition part. Thus, an excess vitrification solution was easily spread out with an edge of the pipette, and the excess vitrification solution was easily removed. In each of the devices for cryopreservation of Examples 3 to 5 having a preservation solution absorber, the vitrify preservation solution was absorbed by the preservation solution absorber in the dropwise attachment as in Comparative Example 2, so that attachment to the surface of the deposition part was generally easily performed. In addition, there was no need for removing an excess preservation solution using a pipette or the like. Thus, the operability during the freezing procedure was generally good.

<Sphere Thawing Procedure and Releasability Evaluation>

The devices for cryopreservation of Examples 1 to 5 and Comparative Examples 1 and 2 each holding a sphere were taken out from the liquid nitrogen, and immersed in a 37° C. thawing solution (a solution prepared by adding 1 M sucrose to the 199 medium used as a base solution). The state of the sphere after immersion was observed under a transmission optical microscope, and the releasability of the sphere was evaluated according to the following criteria. The results are shown in the section "Cell or tissue releasability" in Table 1.

The cell or tissue releasability was evaluated according to the following criteria.

Excellent: After the device for cryopreservation was immersed in the thawing solution, the sphere was released in less than 30 seconds by gently shaking the handle.

Good: After the device for cryopreservation was immersed in the thawing solution, the sphere was released within 30 to 60 seconds by gently shaking the handle.

Acceptable: The sphere was not released within 60 seconds by gently shaking the handle. The sphere was released by rather vigorously shaking the handle.

Poor: The sphere was not released within 60 seconds by gently shaking the handle. The sphere was not released even by rather vigorously shaking the handle.

TABLE 1

|  | Cell or tissue releasability |
| --- | --- |
| Example 1 | Excellent |
| Example 2 | Excellent |
| Example 3 | Good |
| Example 4 | Good |
| Example 5 | Good |
| Comparative Example 1 | Acceptable |
| Comparative Example 2 | Poor |

The results show that the devices for cryopreservation of the present invention enable easy removal of an excess preservation solution surrounding the cell or tissue attached dropwise to the deposition part, and allows the cell or tissue to be reliably held on the surface of the deposition part in the freezing procedure. The devices for cryopreservation further enable quick recovery of the cell or tissue in the thawing procedure.

Example 6

Figure 14:
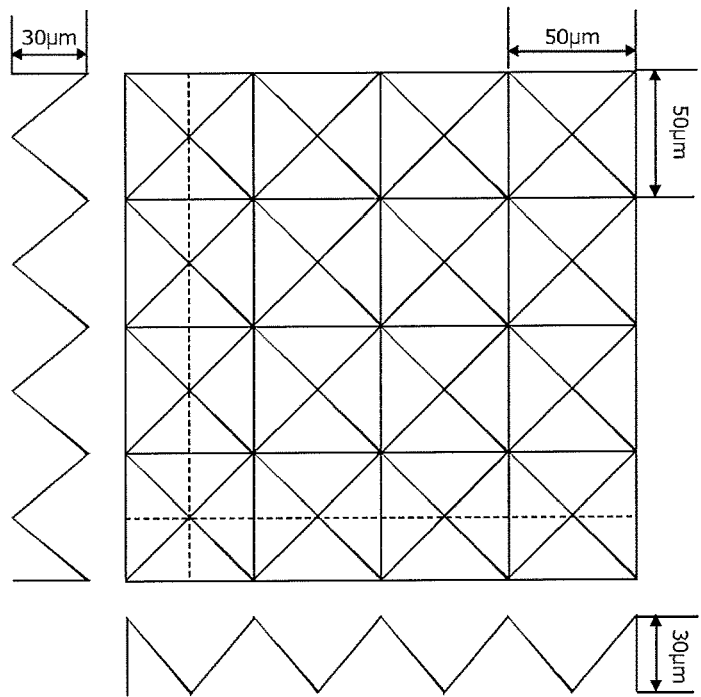
FIG. 14 is a view showing an exemplary mold used in examples.

A polyethylene terephthalate film Lumirror® T60 (thickness 188 µm, total light transmittance 91%) available from Toray Industries, Inc. was provided. The polyethylene terephthalate film was press-molded in a female mold (13 cm×12 cm, overall thickness 130 µm) shown in FIG. 14 in which four-sided pyramid-shaped structures each having a side length of 50 µm and a height of 30 µm are continuously formed, using a roller type embossing machine EMBOSTAR® available from Saito Endiniazu Inc. Thus, protrusions were formed on one side of the polyethylene terephthalate film. The machine is an embossing machine that forms protrusions and recesses by allowing a processing target to pass between the two rollers whose gap is adjustable. The depth of processing to be performed on the processing target can be adjusted by adjusting the gap between the rollers or the processing temperature. In Example 6, the gap between rollers was 320 µm. The processing temperature (measured on the outermost surface of the roller by a contact type thermometer) was 240° C. The protrusions formed on the polyethylene terephthalate film processed under the above conditions each had a height of 5 µm with a pattern pitch of 50 µm. The polyethylene terephthalate film having protrusions and recesses was cut into a rectangle having a size of 1.5 mm (short side)×25.0 mm (long side), and the cut piece was bonded to an ABS resin handle, whereby a device for cryopreservation of Example 6 having a configuration shown in FIG. 1 was produced.

Example 7

A device for cryopreservation of Example 7 was produced as in Example 6, except that the gap between rollers was set to 310 µm for press molding. In Example 7, the protrusions formed on the polyethylene terephthalate film each had a height of 14 µm with a pattern pitch of 50 µm.

Example 8

A device for cryopreservation of Example 8 was produced as in Example 6, except that the gap between rollers was set to 300 µm for press molding. In Example 8, the protrusions formed on the polyethylene terephthalate film each had a height of 22 µm with a pattern pitch of 50 µm.

Example 9

A device for cryopreservation of Example 9 was produced as in Example 6, except that the gap between rollers was set to 290 µm for press molding. In Example 9, the protrusions formed on the polyethylene terephthalate film each had a height of 27 µm with a pattern pitch of 50 µm.

Example 10

Figure 15:
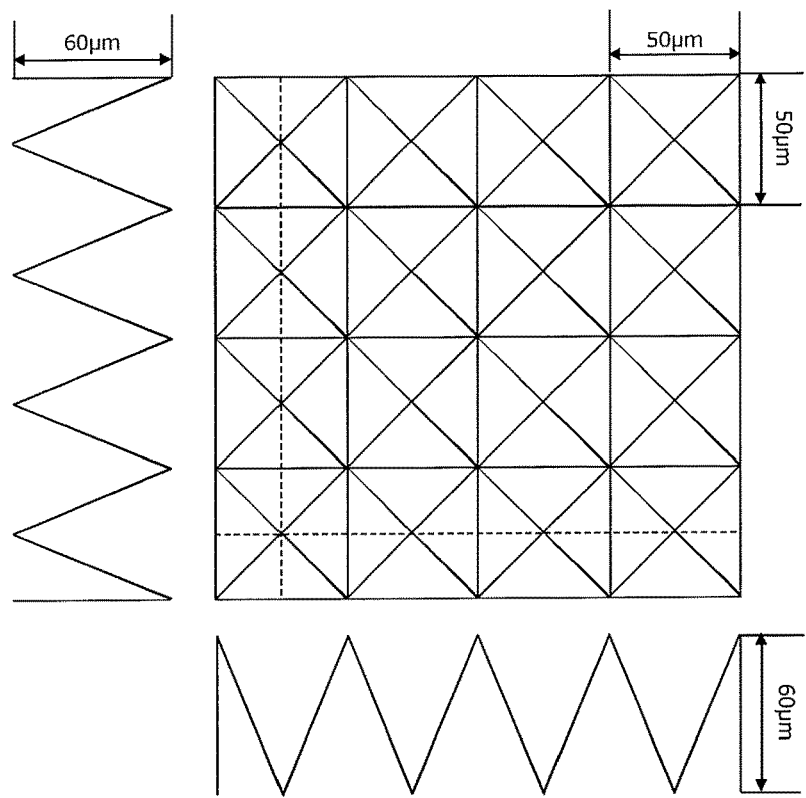
FIG. 15 is a view showing another exemplary mold used in the examples.

A device for cryopreservation of Example 10 was produced as in Example 6, except that a female mold (13 cm×12 cm, overall thickness 300 µm) shown in FIG. 15 in which four-sided pyramid-shaped structures each having a side length of 50 µm and a height of 60 µm are continuously formed was used and the gap between rollers was set to 450 µm for press molding. In Example 10, the protrusions formed on the polyethylene terephthalate film each had a height of 46 µm with a pattern pitch of 50 µm.

Comparative Example 3

A polyethylene terephthalate film Lumirror® T60 (thickness 188 µm) available from Toray Industries, Inc. was cut into a rectangle having a size of 1.5 mm (short side)×25.0 mm (long side), and the cut piece was bonded to an ABS resin handle, whereby a device for cryopreservation of Comparative Example 3 having a configuration shown in FIG. 1 was produced.

<Mouse Egg Freezing Procedure>

Mouse eggs each having a diameter of 100 µm were immersed in a Vit Kit equilibrium solution (liquid temperature 15° C.) available from Irvine Scientific. After immersion in the equilibrium solution, the mouse eggs were immersed in a Vit Kit vitrification solution (liquid temperature 4° C.) available from Irvine Scientific. After immersion in the vitrification solution for 90 seconds, a single mouse egg was deposited on the deposition part of each of the devices for cryopreservation (Examples 6 to 10 and Comparative Example 3) using a pipette under a transmission microscope. An excess vitrification solution present in the deposition part was removed by pipetting. Subsequently, the devices for cryopreservation were immersed in liquid nitrogen and vitrified. The frozen devices for cryopreservation were stored in a liquid nitrogen storage container.

<Mouse Egg Thawing Procedure and Releasability Evaluation>

The devices for cryopreservation (Examples 6 to 10 and Comparative Example 3) each holding a mouse egg were taken out from the liquid nitrogen, and immersed in a 37° C. Vit Kit thawing solution available from Irvine Scientific. The state of the mouse egg being released in the thawing solution from the deposition part of each device for cryopreservation was observed under transmission optical microscope, and evaluated according to the following criteria. Table 2 shows evaluation results.

Excellent: When the device for cryopreservation was immersed in the thawing solution, the mouse egg was released in less than 30 seconds by gently shaking the handle.

Good: When the device for cryopreservation was immersed in the thawing solution, the mouse egg was released within 30 to 60 seconds by gently shaking the handle.

Acceptable: When the device for cryopreservation was immersed in the thawing solution, the mouse egg was not released by gently shaking the handle. The mouse egg was released by vigorously shaking the handle.

Poor: When the device for cryopreservation was immersed in the thawing solution, the mouse egg was not released by gently or vigorously shaking the handle.

TABLE 2

|  | Cell or tissue releasability |
| --- | --- |
| Example 6 | Excellent |
| Example 7 | Excellent |
| Example 8 | Excellent |
| Example 9 | Excellent |
| Example 10 | Good |
| Comparative Example 3 | Acceptable |

<Preparation of Spheres>

Spheres for use in the cell or tissue releasability evaluation were prepared as follows. Mouse embryonic fibroblasts were cultured on a cell culture petri dish, and the fibroblasts were released and recovered by trypsin. Subsequently, the cells were seeded on PrimeSurface® 96 U plate available from Sumitomo Bakelite Co., Ltd. at a cell concentration of 50 cells/well, followed by suspension culture, whereby sphere formation was induced. After culturing for about 40 hours, spheres each having a diameter of about 50 μm were obtained.

<Sphere Freezing Procedure>

The spheres each having a diameter of 50 μm were immersed in a Vit Kit equilibrium solution (liquid temperature 15° C.) available from Irvine Scientific. After immersion in the equilibrium solution, the spheres were immersed in a Vit Kit® vitrification solution (liquid temperature 4° C.) available from Irvine Scientific. After immersion in the vitrification solution for 90 seconds, a single sphere was deposited on the deposition part of each of the devices for cryopreservation (Examples 6 to 10 and Comparative Example 3) using a pipette under a transmission microscope. An excess vitrification solution present in the deposition part was removed by pipetting. Subsequently, the devices for cryopreservation were immersed in liquid nitrogen and vitrified. The frozen devices for cryopreservation were stored in a liquid nitrogen storage container.

<Sphere Thawing Procedure and Releasability Evaluation>

The devices for cryopreservation (Examples 6 to 10 and Comparative Example 3) each holding a sphere were taken out from the liquid nitrogen, and immersed in a 37° C. Vit Kit thawing solution available from Irvine Scientific. The state of the sphere being released in the thawing solution from each device for cryopreservation was observed under transmission optical microscope, and evaluated according to similar criteria as those for the releasability evaluation described above. Table 3 shows evaluation results.

TABLE 3

|  | Cell or tissue releasability |
| --- | --- |
| Example 6 | Good |
| Example 7 | Good |
| Example 8 | Good |
| Example 9 | Acceptable |
| Example 10 | Acceptable |
| Comparative Example 3 | Poor |

Example 11

Porous polytetrafluoroethylene (pore size 0.2 μm, porosity 71%, thickness 35 μm) available from Advantec Toyo Kaisha, Ltd. was cut into a strip having a size of 20 cm×10 cm, using a lever cutter. Then, the cut piece of the porous body was placed on a polycarbonate film having a thickness of 300 μm. The female mold (13 cm×12 cm, overall thickness 130 μm) shown in FIG. 14 in which four-sided pyramid-shaped structures each having a side length of 50 μm and a height of 30 μm are continuously formed was placed on the porous body placed on the polycarbonate film, and protrusions and recesses were formed on the porous body, with a gap between rollers of 510 μm at a processing temperature of 40° C. Separately, a polyethylene terephthalate film Lumirror® T60 (thickness: 188 μm) available from Toray Industries, Inc. which had been subjected to easy adhesion treatment was provided as a support. Onto the support was applied hot melt urethane resin Purmelt® QR 170-7141P (Henkel Japan Ltd.) as an adhesive layer to achieve a dry solids content of 30 g/m². Subsequently, the polycarbonate film and the mold were separated from the porous body including protrusions and recesses, and a surface of the porous body on the side not having protrusions or recesses was bonded to the adhesive layer side of the polyethylene terephthalate film before the adhesive layer was completely solidified. The resulting bonded product was cut into a rectangle having a size of 1.5 mm (short side)× 25.0 mm (long side), and the cut piece was bonded to an ABS resin handle, whereby a device for cryopreservation of Example 11 was produced. In Example 11, the protrusions formed on the porous body each had a height of 3 μm with a pattern pitch of 50 μm.

Example 12

A device for cryopreservation of Example 12 was produced as in Example 11, except that the gap between rollers was set to 490 μm for press molding. In Example 12, the protrusions formed on the porous body each had a height of 5 μm with a pattern pitch of 50 μm.

Example 13

A device for cryopreservation of Example 13 was produced as in Example 11, except that the gap between rollers was set to 470 μm for press molding. In Example 13, the protrusions formed on the porous body each had a height of 9 μm with a pattern pitch of 50 μm.

Example 14

A device for cryopreservation of Example 14 was produced as in Example 11, except that the gap between rollers was set to 450 μm for press molding. In Example 14, the protrusions formed on the porous body each had a height of 12 μm with a pattern pitch of 50 μm.

Example 15

A device for cryopreservation of Example 15 was produced as in Example 11, except that the gap between rollers was set to 430 μm for press molding. In Example 15, the protrusions formed on the porous body each had a height of 16 μm with a pattern pitch of 50 μm as observed under an electronic microscope.

Example 16

Figure 16:
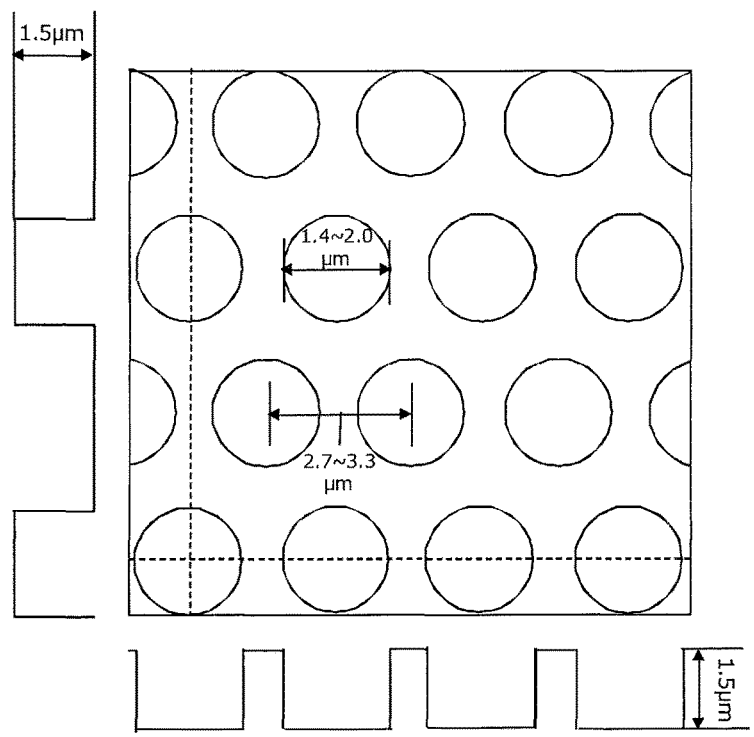
FIG. 16 is a view showing still another exemplary mold used in the examples.

A device for cryopreservation of Example 16 was produced as in Example 11, except that a female mold (external dimensions 13 cm×13 cm (pattern formation area 7 cm×7 cm), overall thickness 190 μm) shown in FIG. 16 in which cylindrical structures having a diameter of 1.4 to 2.0 μm are continuously formed with a pattern pitch of 2.7 to 3.3 μm was used and the gap between rollers was set to 540 μm for press molding. In Example 16, the protrusions formed on the porous body each had a height of 1.2 μm with a pattern pitch of 3.0 μm.

Example 17

Figure 17:
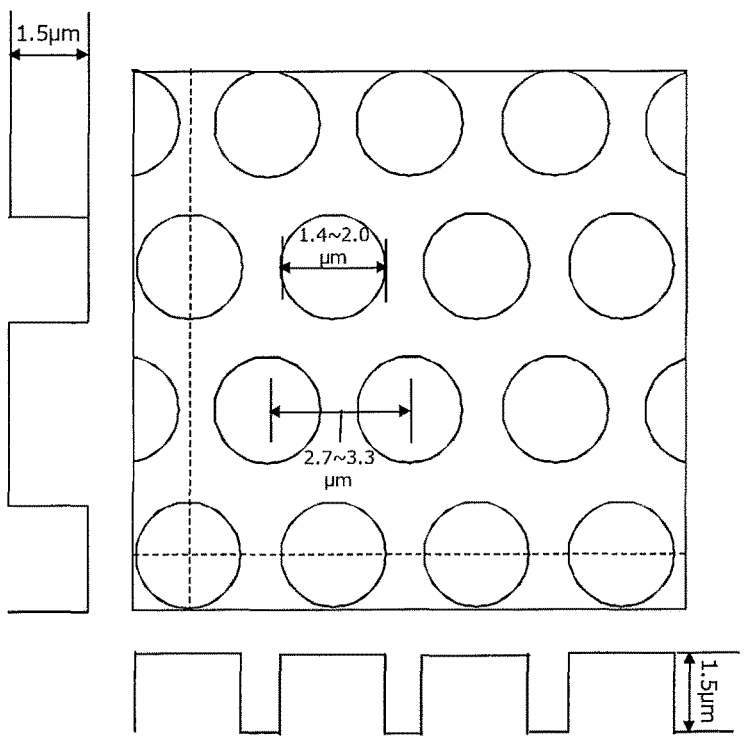
FIG. 17 is a view showing still another exemplary mold used in the examples.

A device for cryopreservation of Example 17 was produced as in Example 16, except that a male mold (external dimensions 13 cm×13 cm (pattern formation area 7 cm×7 cm), overall thickness 190 μm) shown in FIG. 17 in which cylindrical structures having a diameter of 1.4 to 2.0 μm are continuously formed with a pattern pitch of 2.7 to 3.3 μm was used, instead of the female mold shown in FIG. 16, for press molding. In Example 17, the protrusions formed on the porous body each had a height of 1.1 μm with a pattern pitch of 3.0 μm.

Example 18

A device for cryopreservation of Example 18 was produced in a similar manner, except that a soluble layer was provided on the deposition part of the device for cryopreservation produced in Example 11. The soluble layer was provided by dip coating the bonded product with a 2 mass % aqueous solution of GOHSENX® WO-320R (degree of saponification 88.3 mol %) available from The Nippon Synthetic Chemical Industry Co., Ltd., followed by drying at room temperature and heating at 120° C. for 40 hours. In Example 18, the protrusions formed on the porous body each had a height of 2.9 μm with a pattern pitch of 50 μm.

Example 19

A device for cryopreservation of Example 19 was produced as in Example 18 by providing a soluble layer on the deposition part of the device for cryopreservation produced in Example 12. In Example 19, the protrusions formed on the porous body each had a height of 4.9 μm with a pattern pitch of 50 μm.

Comparative Example 4

A device for cryopreservation of Comparative Example 4 was produced as in Example 11, except that a porous polytetrafluoroethylene available from Advantec Toyo Kaisha, Ltd. not having protrusions was used as the deposition part.

The cell or tissue releasability was evaluated in a similar manner according to similar criteria as those for the cell or tissue releasability using a mouse egg having a diameter of 100 μm described above. Table 4 shows the results.

TABLE 4

|  | Cell or tissue releasability |
| --- | --- |
| Example 11 | Good |
| Example 12 | Good |
| Example 13 | Good |
| Example 14 | Good |
| Example 15 | Good |
| Example 16 | Good |
| Example 17 | Good |
| Example 18 | Excellent |
| Example 19 | Exellent |
| Comparative Example 4 | Poor |

Results in Tables 2 to 4 show that the present invention can achieve excellent releasability that allows easy release of a cell or tissue during thawing.

Example 20

A transparent PET film (total light transmittance 91%, haze 5.5%) which had been subjected to easy adhesion treatment was provided as a support. Onto the support was applied hot melt urethane resin Purmelt® QR 170-7141P (Henkel Japan Ltd.) as an adhesive layer to achieve a dry solids content of 30 g/m². Before the adhesive layer was completely solidified, a non-roughened surface of a preservation solution absorber whose one surface was roughened by the following method was bonded to the adhesive layer.

The preservation solution absorber whose one surface was roughened was obtained as follows: a fine mold having a surface on which four-sided pyramids each having a side length of 50 μm and a height of 25 μm are arranged in a lattice was pressure or thermally transferred to a 4 cm×8 cm region of porous polytetrafluoroethylene (pore size 0.2 μm, porosity 71%, thickness 35 μm) available from Advantec Toyo Kaisha, Ltd. at a surface pressure of 1.64 kN, a temperature of 120° C., and a pressurizing and heating time of 2 minutes. A surface of the preservation solution absorber including protrusions and the recesses were dip-coated with a 2 mass % aqueous solution of PVA103 (degree of saponification 98.5 mol %) available from Kurary Co., Ltd., followed by drying at room temperature and heating at 120° C. for 40 hours, whereby a soluble layer was formed. The surface of the deposition part had an Ra of 1.69 μm as measured by Surfcom® 1400D available from Tokyo Seimitsu Co., Ltd. The soluble layer had a solids content of 1.6 g/m². The size of the deposition part formed on the support was 1.5 mm×5 mm. Subsequently, the support was bonded to an ABS resin handle, whereby a device for cryopreservation of Example 20 having a configuration shown in FIG. 1 was produced.

Example 21

A device for cryopreservation of Example 21 was produced as in Example 20, except that a soluble layer was not provided on the roughened porous polytetrafluoroethylene in the production of the device for cryopreservation of Example 20. The surface of the deposition part had an Ra of 2.20 μm as measured by Surfcom® 1400D available from Tokyo Seimitsu Co., Ltd.

Example 22

A device for cryopreservation of Example 22 was produced by increasing the surface pressure to 2.87 kN during molding by pressing a heated mold in the production of the device for cryopreservation of Example 20. The surface of the deposition part had an Ra of 3.12 μm as measured by Surfcom® 1400D available from Tokyo Seimitsu Co., Ltd.

<Mouse Embryo Freezing Procedure>

Mouse embryos each having a diameter of about 100 μm was immersed in a 4° C. preservation solution (15 vol % DMSO (dimethyl sulfoxide), 15 vol % ethylene glycol, 14 vol % fetal bovine serum, 56 vol % modified phosphate buffer (137 mM NaCl, 2.7 mM KCl, 0.9 mM $CaCl_2.H_2O$, 0.5 mM $MgCl_2.6H_2O$, 1.5 mM $KH_2PO_4$, 8 mM $Na_2HPO_4$, 5.6 mM glucose, 0.3 mM sodium pyruvate, 65 μg/ml dibekacin sulfate, 1 mg/ml polyvinylpyrrolidone, 14.8 mM L-proline, 200 mM trehalose, 0.5 M sucrose). After immersion in the preservation solution for 30 seconds, a single mouse embryo was deposited on the deposition part of each of the devices for cryopreservation produced. An excess preservation solution around the mouse embryo was removed as much as possible with a pipette under a transmission microscope. The device was then immersed in liquid nitrogen and vitrified. The frozen device for cryopreservation was stored in a liquid nitrogen storage container until thawing.

<Mouse Embryo Thawing Procedure and Releasability Evaluation>

Each device for cryopreservation holding the mouse embryo was taken out from the liquid nitrogen and immersed in a 37° C. thawing solution (a solution prepared by adding 1 M sucrose to the modified phosphate buffer). The mouse embryo thus immersed was observed under a transmission optical microscope, and the releasability of the mouse embryo during thawing was evaluated according to the following criteria. The results are shown in the section "Cell or tissue releasability" in Table 5.

The protrusions formed on the deposition part of the device for cryopreservation used for the mouse embryo freezing procedure, the mouse embryo thawing procedure, and the releasability evaluation had a pitch of 50 μm in each of examples 20 to 22.

The cell or tissue releasability was evaluated according to the following criteria.

Excellent: When the device for cryopreservation was immersed in the thawing solution, the mouse embryo was released by shaking the handle (the time required for the release was less than 20 seconds).

Good: When the device for cryopreservation was immersed in the thawing solution, the mouse embryo was released by shaking the handle (the time required for the release was 20 seconds or longer but less than 40 seconds).

Acceptable: When the device for cryopreservation was immersed in the thawing solution, it took 40 seconds or longer but less than 60 seconds to release the mouse embryo by shaking the handle.

Poor: The mouse embryo was not released within 60 seconds by shaking the handle.

TABLE 5

|  | Cell or tissue releasability |
| --- | --- |
| Example 20 | Excellent |
| Example 21 | Good |
| Example 22 | Excellent |

The results in Table 5 show the devices for cryopreservation of the present invention exhibit excellent releasability during thawing.

INDUSTRIAL APPLICABILITY

The present invention can be applied to cryopreservation of cells or tissues such as cells or tissues for embryo transfer and artificial insemination of domestic animals (e.g., cattle) and other animals, and for human artificial insemination; iPS cells; ES cells; commonly used culture cells; cells or tissues, including embryos and eggs, harvested from living bodies for the purpose of examination or implantation; and cells or tissues cultured in vitro.

REFERENCE SIGNS LIST

1 handle
2 support
3, 3a, 3b, 3c, 3d, 3e, 3f, 3g, 3h deposition part
4 protrusion
5 recess
6 cell
7 preservation solution
8 preservation solution absorber
9, 9a, 9b, 9c device for cryopreservation

The invention claimed is:

1. A device for cryopreservation of a cell or tissue, comprising:
    a deposition part on which a cell or tissue is to be deposited together with a preservation solution,
    wherein a surface of the deposition part includes a protrusion for holding a cell or tissue and a recess for storing a preservation solution, and
    the protrusion for holding the cell or tissue has a height that is 1/100 or more and less than 1/2 of an average diameter of the cell or tissue.

2. The device for cryopreservation of a cell or tissue according to claim 1,
    wherein the surface of the deposition part on which the cell or tissue is to be deposited together with a preservation solution has an arithmetic average roughness Ra of 1.0 μm or more.

3. The device for cryopreservation of a cell or tissue according to claim 1,
    wherein the deposition part has a preservation solution absorber.

4. The device for cryopreservation of a cell or tissue according to claim 2,
    wherein the deposition part has a preservation solution absorber.

* * * * *